(12) United States Patent
Hak

(10) Patent No.: US 6,494,940 B1
(45) Date of Patent: Dec. 17, 2002

(54) AIR PURIFIER

(75) Inventor: Marron Hak, Richmond, VA (US)

(73) Assignee: Hamilton Beach/Proctor-Silex, Inc., Glen Allen, VA (US)

( * ) Notice: Subject to any disclaimer, the term of this patent is extended or adjusted under 35 U.S.C. 154(b) by 0 days.

(21) Appl. No.: 09/676,322

(22) Filed: Sep. 29, 2000

(51) Int. Cl.$^7$ .......................... B01D 35/30; B01D 50/00
(52) U.S. Cl. ............................ 96/224; 96/397; 96/416; 96/417; 96/421; 55/471; 55/486; 55/491; 55/DIG. 34
(58) Field of Search .......................... 55/467, 471, 486, 55/491, 495, DIG. 34; 96/224, 413, 416, 417, 418, 421, 397; 116/DIG. 25

(56) References Cited

U.S. PATENT DOCUMENTS

| | | |
|---|---|---|
| 2,335,056 A | 11/1943 | Grison |
| 2,638,644 A | 5/1953 | Rauhut |
| D189,420 S | 12/1960 | Diehl |
| 3,024,655 A * | 3/1962 | Dwyer et al. .......... 55/DIG. 34 |
| D193,139 S | 7/1962 | Karp |
| D216,794 S | 3/1970 | Patrick |
| 3,518,046 A * | 6/1970 | Cicirello ...................... 96/224 |
| 3,600,590 A | 8/1971 | Einstein |
| 3,745,750 A | 7/1973 | Arff |
| 3,757,495 A | 9/1973 | Sievers |
| 3,860,818 A | 1/1975 | Stalder et al. |
| D234,606 S | 3/1975 | Gamble |
| 3,936,284 A | 2/1976 | Mason |
| 3,948,445 A | 4/1976 | Andeweg |
| 4,004,361 A | 1/1977 | McVeety |
| 4,040,568 A | 8/1977 | Mason, Jr. et al. |
| 4,118,191 A | 10/1978 | Böhnensieker |
| 4,210,429 A | 7/1980 | Golstein |
| 4,214,146 A | 7/1980 | Schimanski |
| 4,504,290 A | 3/1985 | Pontius |
| 4,605,425 A | 8/1986 | Verrando et al. |
| 4,666,638 A | 5/1987 | Baker et al. |

(List continued on next page.)

FOREIGN PATENT DOCUMENTS

| | | | |
|---|---|---|---|
| JP | 3254808 A | * | 11/1991 |
| WO | 9747928 | | 10/1997 |

*Primary Examiner*—Robert A. Hopkins
(74) *Attorney, Agent, or Firm*—Akin, Gump, Strauss, Hauer & Feld, L.L.P.

(57) ABSTRACT

An air purifier including a housing supporting an air inlet, an air outlet and an air flow passage interconnecting the air inlet and the air outlet. The airflow passage is defined by a filtration chamber positioned upstream from a blower chamber and an ultraviolet light chamber. A blower assembly is supported within the blower chamber and includes a fan driven by a motor for forcing air through the air flow passage from the air inlet to the air outlet. A pre-filter and a main filter are removably supported within the air filtration chamber for entrapping particulates having a size of 0.3 microns and greater. An ultraviolet light source is positioned within the light chamber and is positioned proximate the air outlet. An outlet grille is supported proximate the air outlet and provides for the passage of air while substantially preventing the passage of ultraviolet light. The outlet grille includes a louver assembly including a plurality of blades defining a plurality of convoluted passages. An outlet safety switch is selectively engagable with the outlet grille for preventing operation of the ultraviolet light and the blower assembly if the outlet grille is not properly positioned relative to the housing. An air quality sensor is supported by the housing and provides an indication of ambient air quality to a controller which, in turn, varies operation of the blower assembly based upon the indicated ambient air quality. A filter check gauge is removably positioned proximate the air outlet for providing an indication of air flow volume and thereby, the need to replace either the pre-filter or the main filter.

19 Claims, 16 Drawing Sheets

U.S. PATENT DOCUMENTS

| | | |
|---|---|---|
| 4,701,195 A | 10/1987 | Rosendall |
| 4,719,662 A | 1/1988 | Horak et al. |
| 4,737,173 A | 4/1988 | Kudirka et al. |
| 4,737,174 A | 4/1988 | Pontius |
| 4,743,406 A | 5/1988 | Steiner et al. |
| 4,792,345 A | 12/1988 | Abe et al. |
| 4,839,014 A | 6/1989 | Park et al. |
| 4,849,862 A | 7/1989 | Diskin et al. |
| 4,859,220 A | 8/1989 | Leber et al. |
| 4,917,862 A | 4/1990 | Kraw et al. |
| D308,415 S | 6/1990 | Kunze |
| 4,931,224 A | 6/1990 | Holzner, Sr. |
| 4,937,912 A | 7/1990 | Kurz |
| 5,014,338 A | 5/1991 | Glucksman |
| 5,036,698 A | 8/1991 | Conti |
| 5,061,296 A | 10/1991 | Sengpiel et al. |
| D324,098 S | 2/1992 | Ragonesi |
| 5,089,144 A | 2/1992 | Ozkahyaoglu et al. |
| 5,111,529 A | 5/1992 | Glucksman |
| 5,112,370 A | 5/1992 | Gazzano |
| 5,131,932 A | 7/1992 | Glucksman |
| 5,139,546 A | 8/1992 | Novobilski |
| 5,163,202 A | 11/1992 | Kawakami et al. |
| D335,702 S | 5/1993 | Chang |
| 5,210,818 A | 5/1993 | Wang |
| 5,230,723 A | 7/1993 | Travis et al. |
| 5,236,477 A | 8/1993 | Koketsu |
| 5,240,478 A | 8/1993 | Messina |
| 5,250,232 A | 10/1993 | Pepper et al. |
| 5,266,004 A | 11/1993 | Tsumurai et al. |
| D345,010 S | 3/1994 | Aronsson et al. |
| 5,330,722 A | 7/1994 | Pick et al. |
| 5,378,254 A | 1/1995 | Maly et al. |
| D357,330 S | 4/1995 | Wong et al. |
| 5,407,469 A | 4/1995 | Sun |
| D360,028 S | 7/1995 | Matsuda |
| 5,547,615 A | 8/1996 | Jané et al. |
| D374,713 S | 10/1996 | Ford et al. |
| D377,213 S | 1/1997 | Wang |
| 5,601,636 A | 2/1997 | Glucksman |
| 5,611,967 A | 3/1997 | Jane et al. |
| 5,616,172 A | 4/1997 | Tuckerman et al. |
| D379,220 S | 5/1997 | Ellwood |
| 5,656,242 A | 8/1997 | Morrow et al. |
| 5,679,137 A | 10/1997 | Erdman et al. |
| D390,940 S | 2/1998 | Chen |
| 5,735,918 A | 4/1998 | Barradas |
| D394,100 S | 5/1998 | Promseeda |
| D395,146 S | 6/1998 | Miller et al. |
| 5,762,667 A | 6/1998 | Pippel et al. |
| 5,772,732 A | 6/1998 | James et al. |
| D396,275 S | 7/1998 | Pearson |
| 5,783,117 A | 7/1998 | Byassee et al. |
| 5,792,230 A | 8/1998 | Moore et al. |
| 5,800,583 A | 9/1998 | Pippel et al. |
| 5,800,741 A | 9/1998 | Glenn et al. |
| 5,803,940 A | 9/1998 | Rick et al. |
| 5,810,908 A | 9/1998 | Gray et al. |
| 5,811,004 A | 9/1998 | Robertson et al. |
| D399,943 S | 10/1998 | Ko |
| 5,819,367 A | 10/1998 | Imamura |
| D400,661 S | 11/1998 | Ko |
| D400,662 S | 11/1998 | Davis |
| 5,837,207 A | 11/1998 | Summers |
| 5,840,092 A | 11/1998 | Rick et al. |
| D402,022 S | 12/1998 | Termeer et al. |
| D402,746 S | 12/1998 | Clark et al. |
| 5,862,737 A | 1/1999 | Chiu et al. |
| 5,879,435 A | 3/1999 | Satyapal et al. |
| 5,891,399 A | 4/1999 | Owesen |
| 5,893,939 A * | 4/1999 | Rakocy et al. ................ 55/471 |
| D409,741 S | 5/1999 | Yuen-Ming |
| D411,001 S | 6/1999 | Pinchuk |
| 5,914,453 A | 6/1999 | James et al. |
| 5,925,172 A | 7/1999 | Rick et al. |
| 5,925,320 A | 7/1999 | Jones |
| 5,945,038 A | 8/1999 | Anderson |
| 5,948,355 A | 9/1999 | Fujishima et al. |
| 5,968,455 A | 10/1999 | Brickley |
| D416,318 S | 11/1999 | Sato |
| D416,319 S | 11/1999 | Rollins |
| D416,613 S | 11/1999 | Bellil et al. |
| D416,614 S | 11/1999 | Bellil et al. |
| 5,986,555 A | 11/1999 | Hamburger et al. |
| 5,997,619 A | 12/1999 | Knuth et al. |
| 6,013,121 A | 1/2000 | Chiu et al. |
| 6,017,375 A | 1/2000 | Duell et al. |
| D420,732 S | 2/2000 | Gudefin |
| 6,036,757 A | 3/2000 | Gatchell et al. |
| 6,045,596 A | 4/2000 | Holland, Jr. et al. |
| 6,051,144 A | 4/2000 | Clack et al. |
| 6,053,968 A | 4/2000 | Miller |
| D426,293 S | 6/2000 | Tounsi et al. |
| 6,293,983 B1 * | 9/2001 | More ........................ 55/486 |
| 6,328,791 B1 * | 12/2001 | Pillion et al. ................ 96/418 |

* cited by examiner

AIR PURIFIER

BACKGROUND OF THE INVENTION

1. Field of the Invention

The present invention relates generally to an air purifier and, more particularly, to an air purifier for removing particulates and for sterilizing or killing micro-organisms from ambient air during a plurality of stages.

2. Description of the Related Art

Air contamination by pollen, mold, smoke, dust, pet dander, micro-organisms or any other of a number of known irritants, is a common and long-standing problem. Contact with these contaminants is almost inevitable and often makes breathing uncomfortable for individuals. Moreover, such contaminants may present long-term health risks, particularly for those individuals suffering from allergies, asthma, emphysema and other respiratory related illnesses.

A wide variety of air purifiers are presently available on the market for removing contaminants from ambient air. These systems typically include a fan for circulating air and a mechanical filter disposed in an air path so as to filter or otherwise purify air flowing therethrough. One type of mechanical filter which has gained wide spread acceptance within the industry is a high efficiency particulate air (HEPA) filter which typically entraps particles larger than 0.3 microns in size.

Since many living micro-organisms are smaller than 0.3 microns, they readily pass through such conventional mechanical filters. It is therefore further known to utilize ultraviolet (UV) light produced by ultraviolet lamps to kill micro-organisms, or to sterilize micro-organisms so they will not reproduce.

Ozone may be generated by subjecting air to ultraviolet light. The amount and type of ozone created depends upon the wavelength and intensity of the energy source. While ozone itself has been utilized for the effective sterilization or destruction of micro-organisms, its use is often discouraged due to ozone's inherent health risks to humans. Therefore, it is important that any radiation source utilized to reduce micro-organisms effectively minimizes the human exposure to ozone.

While ultraviolet light sources have been found effective in reducing the number of micro-organisms in ambient air, humans must be properly shielded to avoid prolonged direct exposure to ultraviolet light rays which may cause skin and eye damage, including blindness. Therefore, in traditional air purifiers, the ultraviolet light source is usually positioned in a location within the housing remote from the air inlet and air outlet, or requires the use of reflecting shields to restrict the transmission of ultraviolet light. As such, many traditional air purifiers employing an ultraviolet light source include structures which render the replacement of the ultraviolet lamp a difficult and time consuming task.

Accordingly, there is a need for an air purifier including multiple stages for effectively cleaning ambient air. Moreover, there is a need for such an air purifier including a filter assembly for effectively removing particulates from the air and an ultraviolet light source for sterilizing or killing micro-organisms. Further, there is a need for such an air purifier which provides a structure for facilitating the efficient and convenient replacement of both the filter assembly and the ultraviolet light source, while also preventing potentially harmful human exposure to ultraviolet light rays.

SUMMARY OF THE INVENTION

The air purifier of the present invention includes a housing supporting an air inlet, an air outlet and an air flow passage interconnecting the air inlet and the air outlet. A blower assembly is supported by a dividing wall positioned within the housing and includes a fan driven in rotation by a motor. The blower assembly draws air through the air inlet and then forces the air through the air flow passage from the air inlet to the air outlet. The housing further includes a rear wall and a spacer extending outwardly from the rear wall for maintaining the housing in spaced relation to external objects, such as walls, in order to ensure proper air flow around the air purifier.

A downstream first air filter, or main filter, is disposed within the air flow passage intermediate the air inlet and the blower assembly. A resilient sealing gasket is supported by the main filter for sealingly engaging the dividing wall and thereby preventing air flow from bypassing the main filter. An upstream second air filter, or pre-filter, is removably secured to the main filter and is positioned intermediate the air inlet and the main filter. The main filter preferably comprises a high efficiency particulate air (HEPA) filter adapted for removing particulates of a size 0.3 microns and greater. The pre-filter preferably comprises a carbon mesh filter adapted to remove odors and larger particulates prior to such particulates contacting the main filter.

An ultraviolet light source is disposed downstream from the main filter and the pre-filter, and is positioned within the air flow passage proximate the air outlet. The ultraviolet light source comprises an ultraviolet lamp oriented in a plane substantially perpendicular to the air flow passage to provide maximum ultraviolet light exposure to air passing in proximity thereto.

An outlet grille is supported by the housing proximate the air outlet and is permeable to air and substantially impermeable to ultraviolet light. The outlet grille preferably comprises a louver assembly including a plurality of mutually horizontally spaced and vertically extending blades defining a plurality of convoluted paths or channels for permitting the passage of air from the air flow passage through the air outlet, while substantially preventing the passage of ultraviolet light from the ultraviolet light source through the air outlet. Each blade preferably includes a body having opposing concave and convex surfaces, longitudinally extending side edges and laterally extending end edges. The concave surface of each blade is positioned adjacent the convex surface of an adjacent blade, wherein the side edges of each blade overlap a portion of the body of an adjacent blade.

An outlet safety switch is selectively engagable with the outlet grille. The outlet safety switch is operably connected to the ultraviolet light source and the blower assembly for deactivating both when the outlet grille is not properly positioned relative to the housing. An inlet grille is supported proximate the air inlet and is selectively engagable with an inlet safety switch. The inlet safety switch is likewise operably connected to the ultraviolet light source and the blower assembly for deactivating both when the inlet grille is not properly positioned relative to the housing.

A controller is operably connected to the motor of the blower assembly for controlling the volume of air moving through the air flow passage. An air quality sensor is supported within the housing and includes a sampling chamber, an optical emitter for providing light to the sampling chamber, and an optical receptor communicating with the sampling chamber for detecting light emitted from the optical emitter. The air quality sensor provides an air quality signal to the controller indicative of the air quality within the sampling chamber. The controller adjusts operation of the blower assembly by varying the motor speed in response to the air quality signal.

A cleaning member is removably receivable within the sampling chamber for manually cleaning the optical emitter and the optical receptor. A storage compartment is provided behind the inlet grille for removably storing the cleaning member when it is not in use.

The controller includes a counter, or timer, for determining the cumulative operating time of the air purifier at each of a plurality of motor operating speeds. When each of first predetermined time intervals has elapsed, then the controller provides for a "check pre-filter" indicator signal. Likewise, when each of second predetermined time intervals, greater than each of the first predetermined time intervals, has elapsed then the controller provides for a "check HEPA filter" indicator signal.

A filter check gauge is removably positioned proximate the air outlet for providing an indication of air flow volume. The filter check gauge is removably supported proximate the air outlet for providing an indication of air flow volume therethrough, and more particularly, is supported within a recess formed within the outlet grille. The filter check gauge comprises an open-ended transparent cylindrical tube and an indicator slidably received within the cylindrical tube for moving in response to air flow through the check gauge. A storage compartment is formed behind the inlet grille for removably storing the filter check gauge when it is not in use.

A window is provided within the housing and is in visual communication with the ultraviolet light source for providing the user with an indication of the proper functioning of the ultraviolet light source. The window includes a translucent ultraviolet light filtering cover to protect the user from potentially harmful ultraviolet light rays.

Therefor, it is an object of the present invention to provide a self-contained, portable air purifier.

It is a further object of the present invention to provide such an air purifier including filters for removing particulates and an ultraviolet lamp for sterilizing or killing micro-organisms from ambient air during a plurality of stages.

It is a further object of the present invention to provide an air purifier including easily replaceable filters and an ultraviolet lamp.

It is another object of the present invention to provide an air purifier comprising a plurality of filters including a main filter for entrapping relatively small particulates and a pre-filter for filtering relatively large particulates from ambient air and thereby increasing the effective life span of the main filter.

It is a further object of the present invention to provide such an air purifier including an ultraviolet light source for the sterilization or killing of micro-organisms which pass through upstream filters.

It is still yet another object of the present invention to provide an air purifier including an outlet grille permitting the passage of air but substantially preventing the passage of an ultraviolet light.

It is a further object of the present invention to provide an air purifier including a plurality of interlocking safety switches for preventing inadvertent and potentially harmful exposure to ultraviolet light should the inlet grille or the outlet grille not be properly installed within the air purifier.

It is another object of the present invention to provide a window in visual communication with the ultraviolet light source to permit viewing thereof by a user for verifying proper operation.

It is a further object of the present invention to provide an air quality sensor for sensing ambient air quality and for controlling operation of the air purifier in response thereto.

It is another object of the present invention to provide an automatic filter check indicator signal when a predetermined period of time has elapsed.

It is a further object of the present invention to provide a filter check gauge for simply and efficiently determining air flow volume and the need to replace the air filters.

Other objects and advantages of the invention will be apparent from the following description, the accompanying drawings and the appended claims.

DETAILED DESCRIPTION OF THE PREFERRED EMBODIMENT

Figure 1:
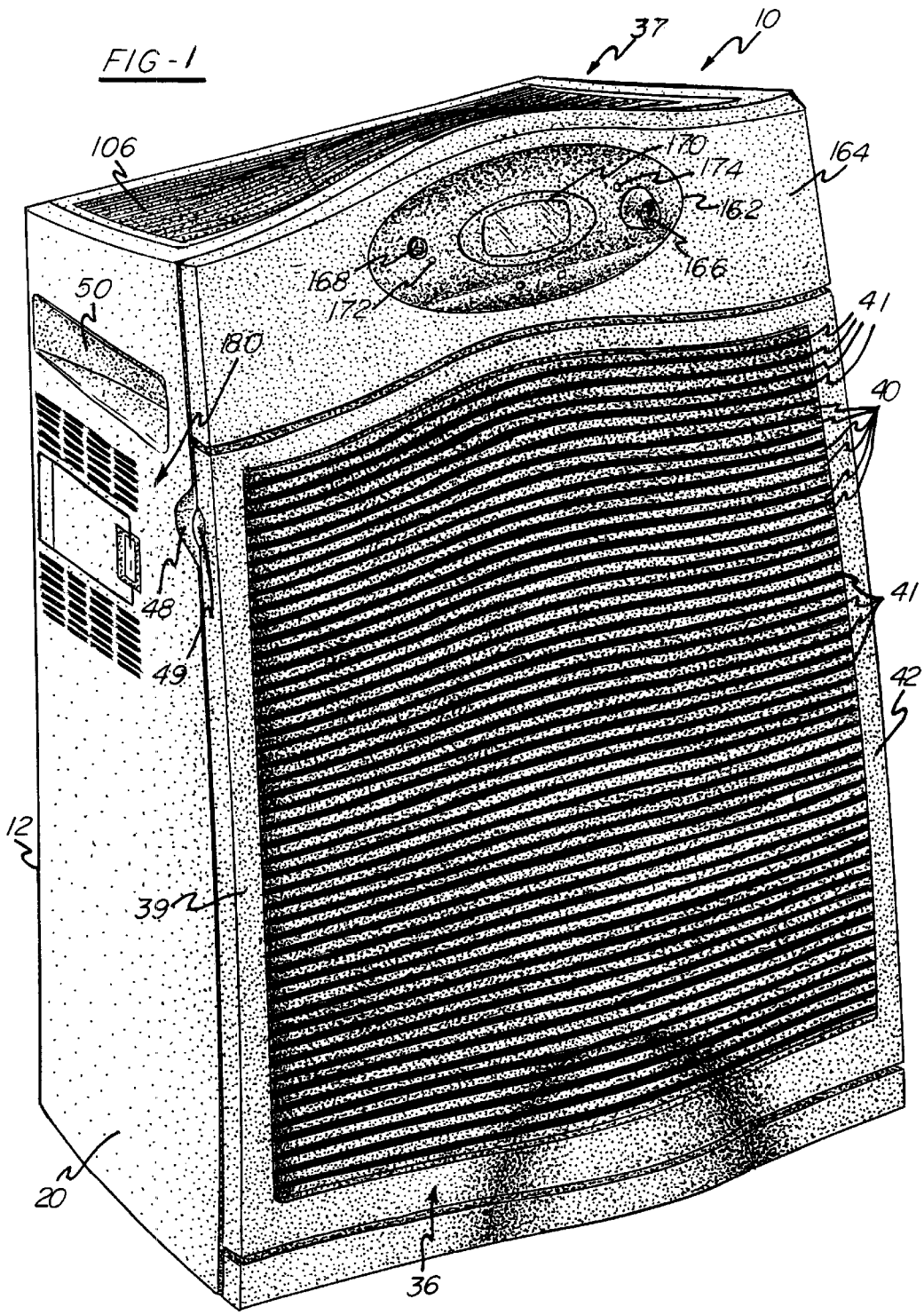
FIG. 1 is a perspective view as seen from the top, front, and left side of an air purifier of the present invention.

Referring initially to FIGS. 1–7, an air purifier 10 made in accordance with the present invention is illustrated as including a housing 12 containing a filtration chamber 14, a blower chamber 16 (FIGS. 6 and 7), and an ultraviolet light chamber 18. Moreover, the housing 12 includes opposing first and second side walls 20 and 22 connected to a rear wall 24. A semi-spherical protuberance or spacer 25 extends outwardly from the rear wall 24 for maintaining the air purifier 10 an appropriate distance from external objects, such as walls, in order to provide adequate air flow.

Figure 2:
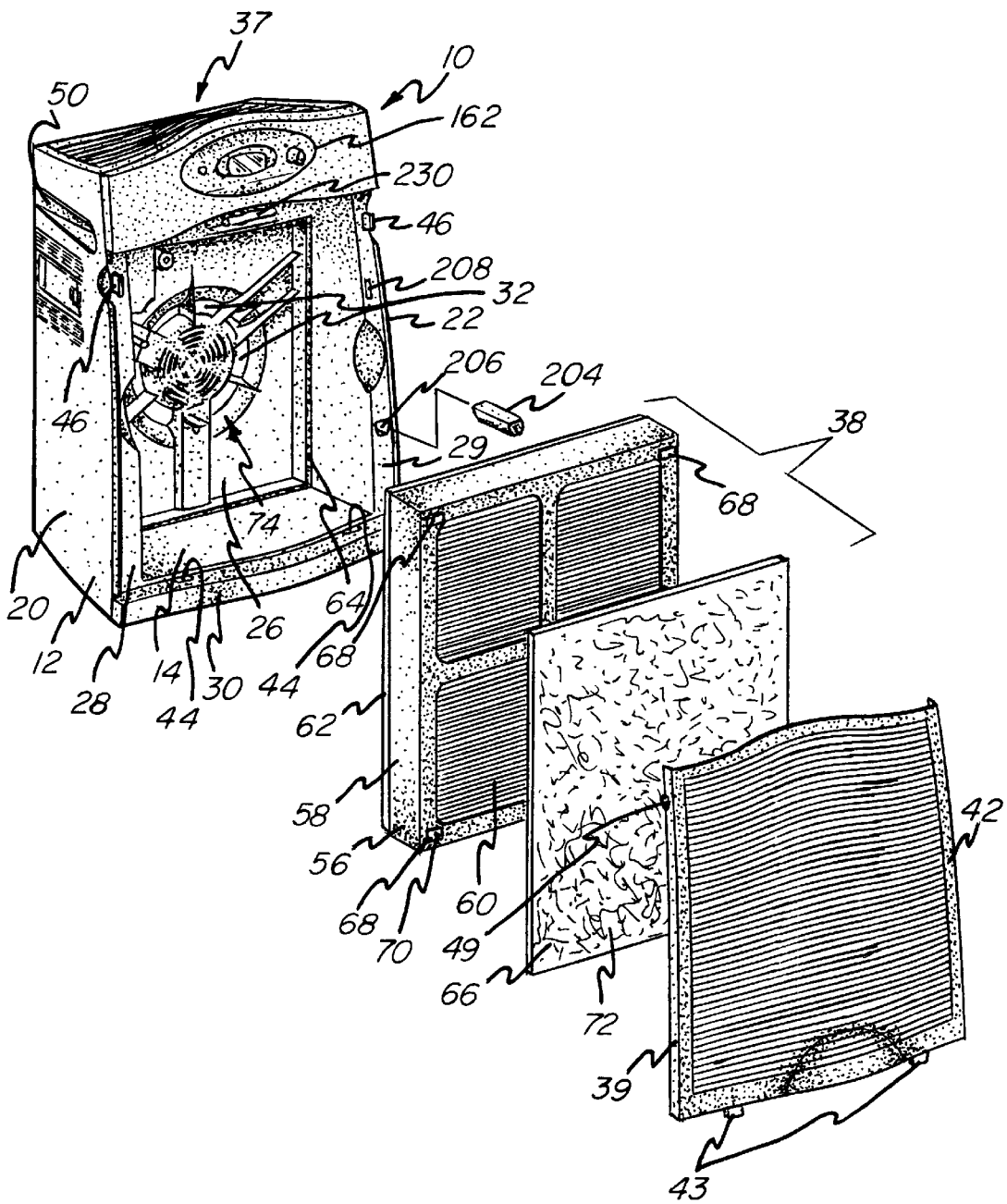
FIG. 2 is an exploded perspective view of an air purifier of the present invention.
Figure 6:
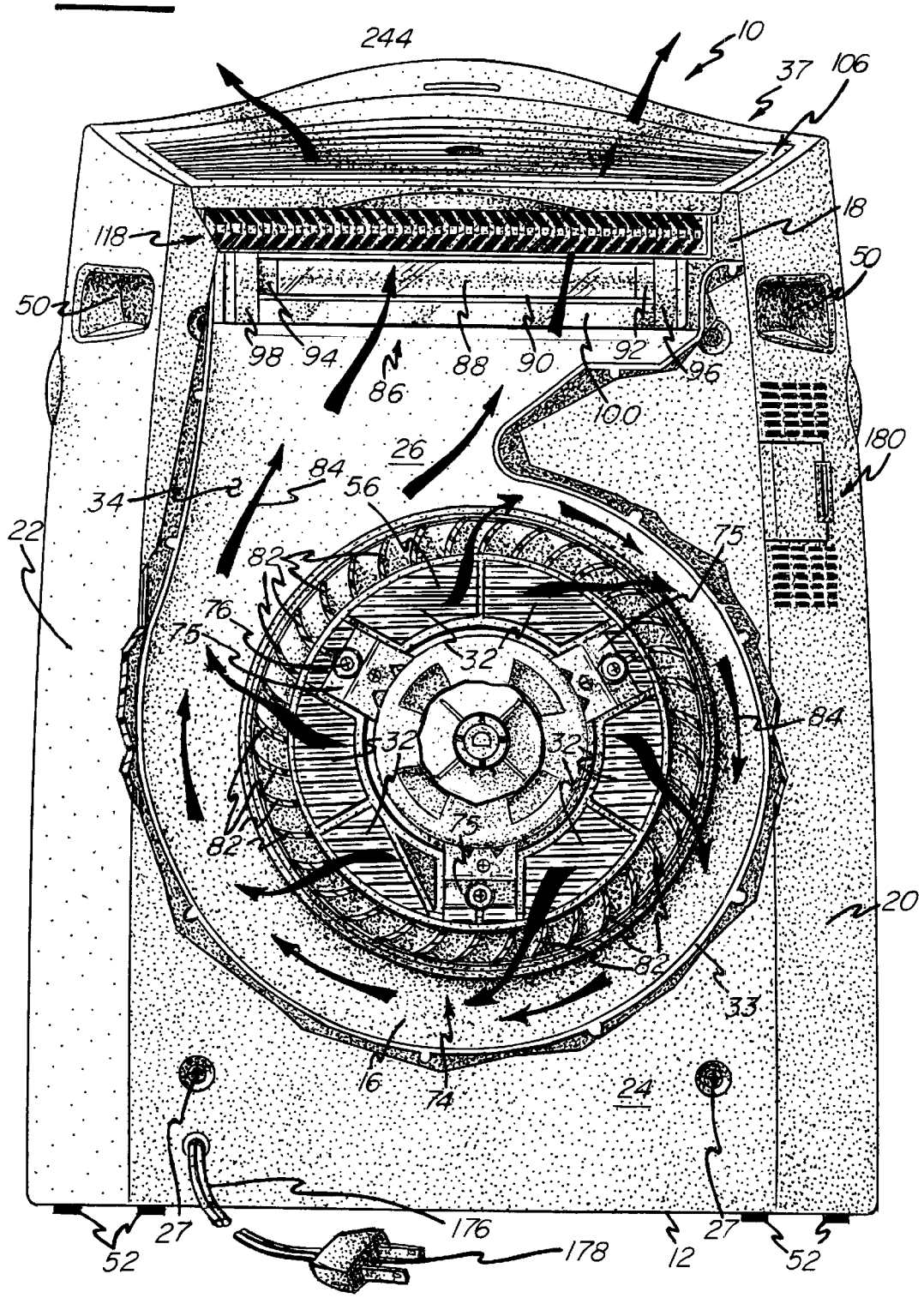
FIG. 6 is a rear elevational view, with a partial cut-away, of the air purifier of the present invention.
Figure 7:
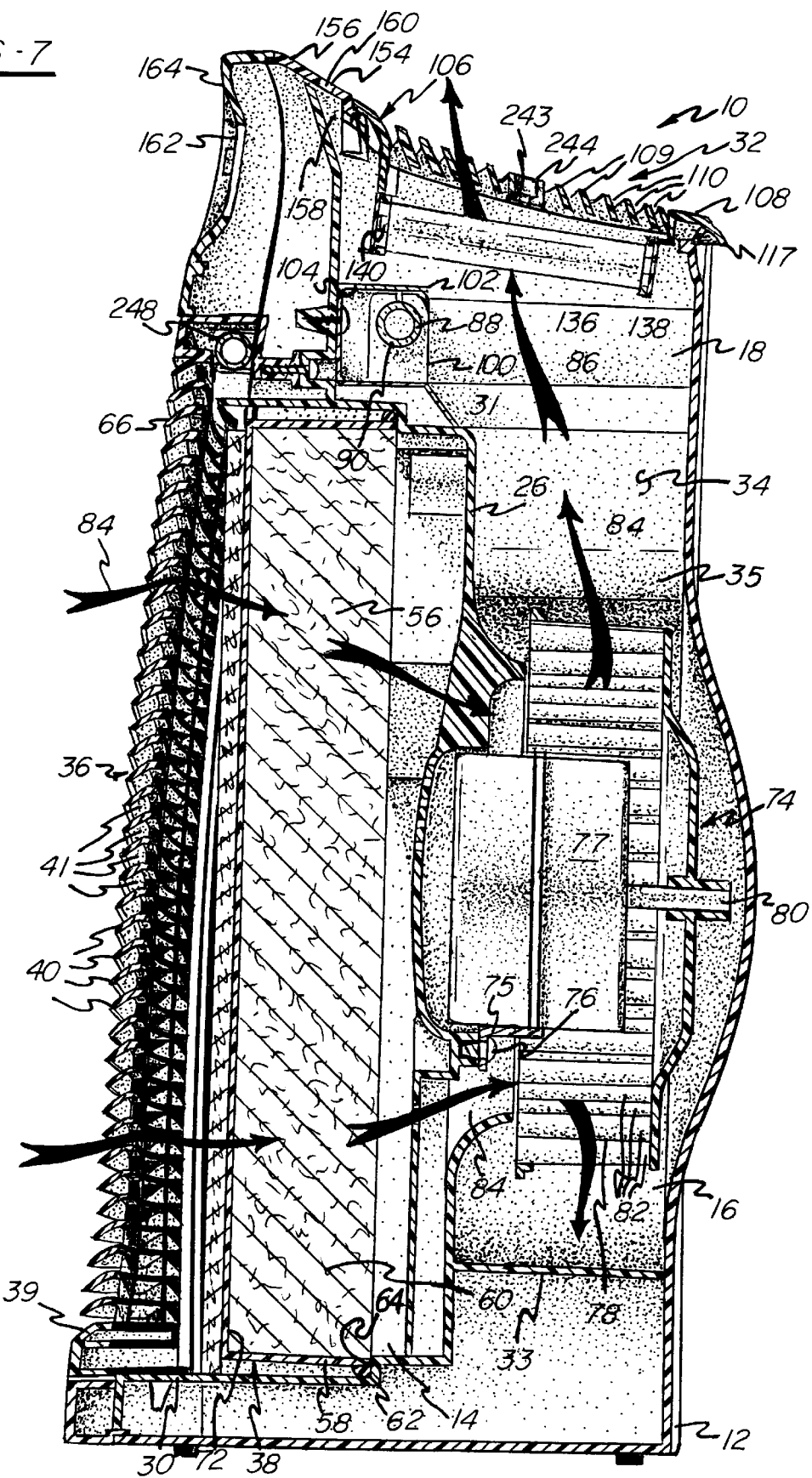
FIG. 7 is a cross-sectional view taken along line 7—7 of FIG. 3.

Referring now to FIGS. 2, 6, and 7, a partition or dividing wall 26 is received within the housing 12 and extends between the opposing side walls 20 and 22 proximate their respective longitudinal center axes. A plurality of bolts 27 (FIG. 6) secure the dividing wall 26 to the rear wall 24 in substantially parallel relation thereto. The dividing wall 26 separates the filtration chamber 14 from the blower chamber 16, thereby defining the rear wall of the filtration chamber 14 and the front wall of the blower chamber 16. The dividing wall 26 supports forwardly extending side walls 28 and 29, bottom wall 30 and top wall 31 (FIG. 7), all received within the housing 12 and which together define the filtration chamber 14.

The dividing wall 26 includes a plurality of openings 32 formed therein for providing communication between the filtration chamber 14 and the blower chamber 16. A baffle or scroll wall 33 extends rearwardly from the dividing wall 26 and abuts with the rear wall 24 of the housing 12 to define the blower chamber 16. The scroll wall 33 is substantially arcuate and extends circumferentially by approximately 270 degrees thereby defining an opening 34 providing communication between the blower chamber 16 and the light chamber 18.

With further reference to FIGS. 1, 2, 4, 6, and 7, the filtration, blower and light chambers 14, 16 and 18, together with openings 32 and 34, define an air passage 35 extending in a downstream direction from an air inlet 36 to an air outlet 37. An air filter assembly 38 is removably supported within the filtration chamber 14 of the air purifier 10.

Figure 10:
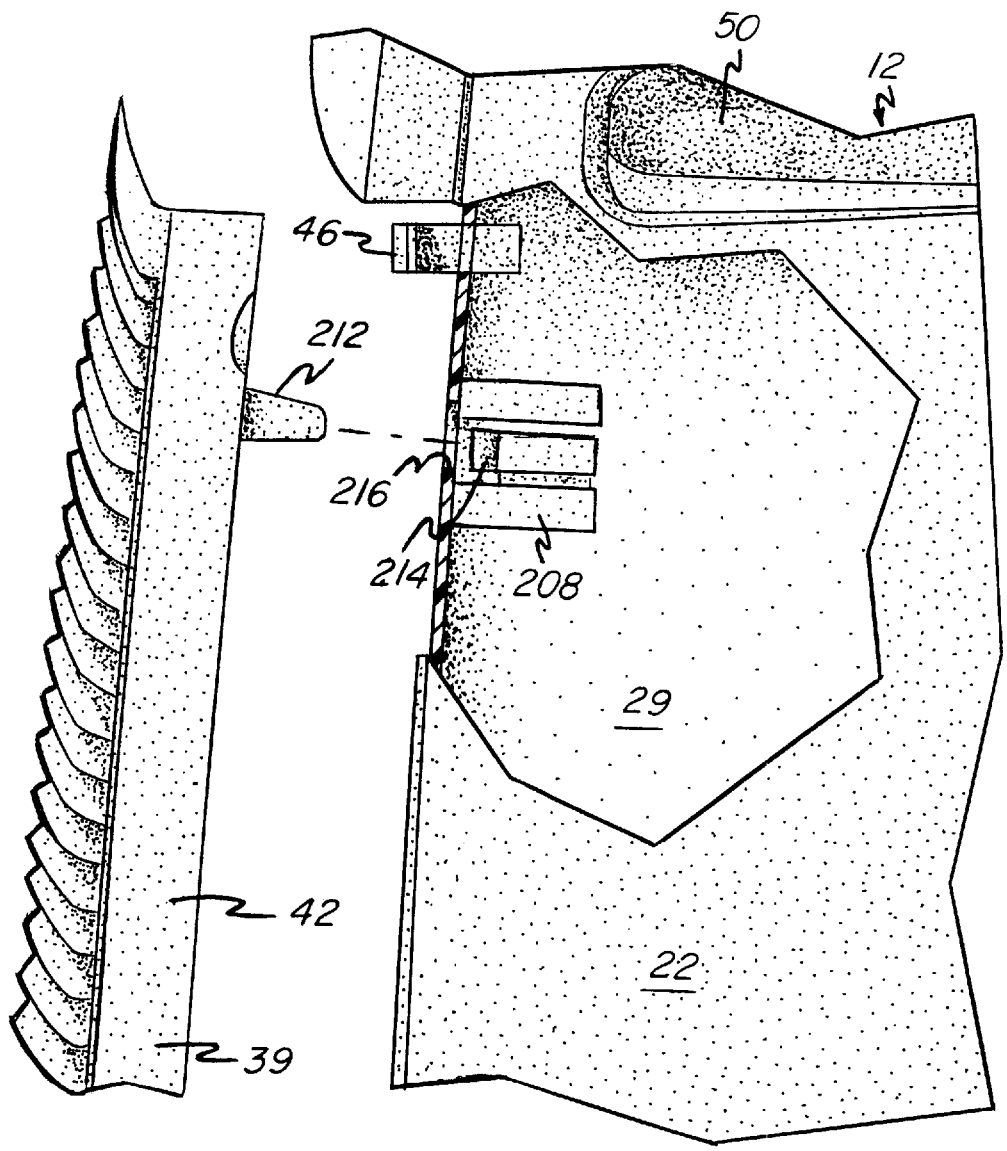
FIG. 10 is a detailed view, with a partial cut-away, of FIG. 4, showing the inlet grille safety switch.

An inlet grille 39 is supported by the side walls 28 and 29 proximate the air inlet 36 and secures the air filter assembly 38 within the filtration chamber 14. The air inlet grille 39 includes a plurality of substantially mutually vertically spaced and horizontally extending blades or slats 40 separating a plurality of slots 41 and supported by a peripheral frame 42. The frame 42 includes downwardly extending positioning tabs 43 receivable within slots 44 formed within the bottom wall 30 (FIG. 2). Self-biased resilient locking tabs 46 are supported by the side walls 28 and 29 for engaging the frame 42 and thereby securing the inlet grille 39 relative to the housing 12 (FIGS. 2 and 10). Recesses 48 are formed within the side walls 20 and 22 of the housing 12 and cooperate with tabs 49 formed within the frame 40 to facilitate removal of the inlet grille 39.

Handle recesses 50 are also formed in the side walls 20 and 22 to assist a user in carrying the air purifier 10. A plurality of feet 52 extend downwardly from a lower wall 54 of the housing 12 for supporting the air purifier 10.

Referring now to FIGS. 2 and 7, the air filter assembly 38 preferably includes a downstream first or main filter 56. The main filter 56 most preferably comprises a high efficiency particulate (HEPA) filter of the type which has been widely utilized in the medical, healthcare and pharmaceutical fields as a mean to entrap airborne particulates in the submicron range. The HEPA filter 56 includes a substantially rigid supporting frame 58 for supporting the filtration material 60. The filtration material 60 is defined to provide a minimum efficiency of 99.97 percent on 0.3 micron size particles, which provides a high degree of filtration in environments where airborne micro-organism concentrations pose a hazard. In addition, the HEPA filter 56 is capable of removing other airborne contaminants such as dust, pollen, mold spores and the like. The HEPA filter 56 is of conventional design and is available from a number of suppliers, including Columbus Industries, Inc. of Ashville, Ohio.

A resilient sealing gasket 62 is positioned on a rear surface of the filter frame 58 and is engagable with a forwardly facing shoulder 64 formed within the dividing wall 26. As may be readily appreciated, by properly positioning the HEPA filter 56 within the filtration chamber 14 with the gasket 62 engaging the shoulder 64, a seal is formed between the filtration chamber 14 and the blower chamber 16 to prevent the undesired passage of particulate around the periphery of the air filter assembly 38.

A second filter or pre-filter 66 is supported upstream from the HEPA filter 56 immediately adjacent the air inlet 36. The pre-filter 66 is of relatively low efficiency and overlies the HEPA filter 56. Moreover, the pre-filter 66 has a particulate retention size much greater than the 0.3 micron size of the HEPA filter 56 for trapping conventional airborne particles such as lint, dust, pollen and the like. The pre-filter 66 preferably includes a carbon for the treatment of odors, fumes and other noxious vapors which may be present in the incoming air flow. The pre-filter 66 performs the important function of removing large particulates before they enter the HEPA filter 56 to extend the life of the HEPA filter 56. As such, the pre-filter 66 is expected to be replaced substantially more frequently than the HEPA filter 56. The pre-filter 66 is of conventional design and is available from a number of suppliers, including Columbus Industries, Inc. of Ashville, Ohio.

Turning again to FIG. 2, a plurality of securing devices 68 are secured to a front surface of the frame 58 of the main filter 56. The securing devices 68 releasably secure the pre-filter 66 to the HEPA filter 56. Each securing device 68 preferably includes a plurality of hooks which releasably engage a plurality of naturally occurring loops formed within the pre-filter 66 in the manner of the well-known VELCRO® hook and loop fastener. As may be readily appreciated, the pre-filter 66 may be simply stretched over the front surface of the frame 58 and then secured in place by the securing devices 68.

With further reference to FIGS. 2, 6, and 7, a blower assembly 74 is supported within the blower chamber 16 by a plurality of conventional brackets 75 fixed to the dividing wall 26 through a conventional fastener, such as bolts 76. The blower assembly 74 includes a conventional motor 77 for driving a centrifugal fan 78 in rotation. The fan 78 includes a shaft 80 substantially coaxially aligned with the air inlet 36 and driven in rotation by the motor 77 for imparting movement to a plurality of arcuate blades 82 extending substantially radially outwardly relative to the shaft 80. As noted above, openings 32 are formed within the dividing wall 26 for permitting air flow between the filtration chamber 14 and blower chamber 16 (FIGS. 2, 6 and 7). As indicated by arrows 84 in FIGS. 6 and 7, the blower assembly 74 draws air axially through the air inlet 36, through the air filter assembly 38 and into the blower chamber 16. The blower assembly 74 discharges the air radially outwardly from the shaft 80 of the fan 78. The discharged air is then directed by the scroll wall 33 upwardly through the opening 34 and into the light chamber 18.

Figure 8:
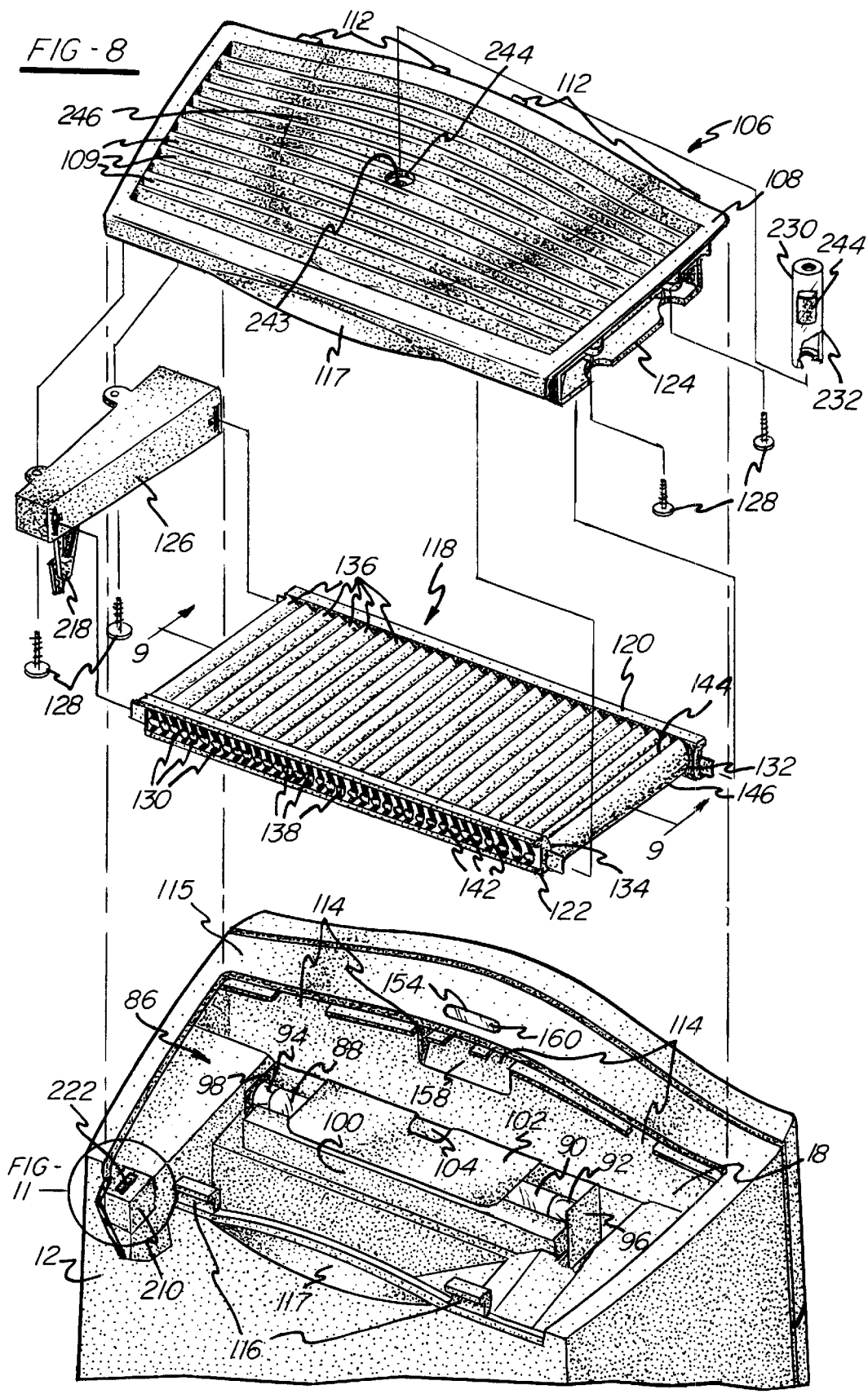
FIG. 8 is a partially exploded perspective view of the top of the air purifier of the present invention.

Turning now to FIGS. 6–8, an ultraviolet (UV) light source 86 is positioned within the light chamber 18 and is oriented in a plane substantially perpendicular to the portion of the air passage 35 through the light chamber 18 in order to maximize the air flow's exposure to ultraviolet light. It should be noted that the cross-sectional area of the light chamber 18 perpendicular to the air flow is greater than the cross-sectional area of the blower chamber 16 intermediate the fan 78 and the scroll wall 33 and perpendicular to the air flow. As such, the air flow velocity decreases upon entering the light chamber 18, thereby increasing exposure time to the light source 86.

Figure 14:
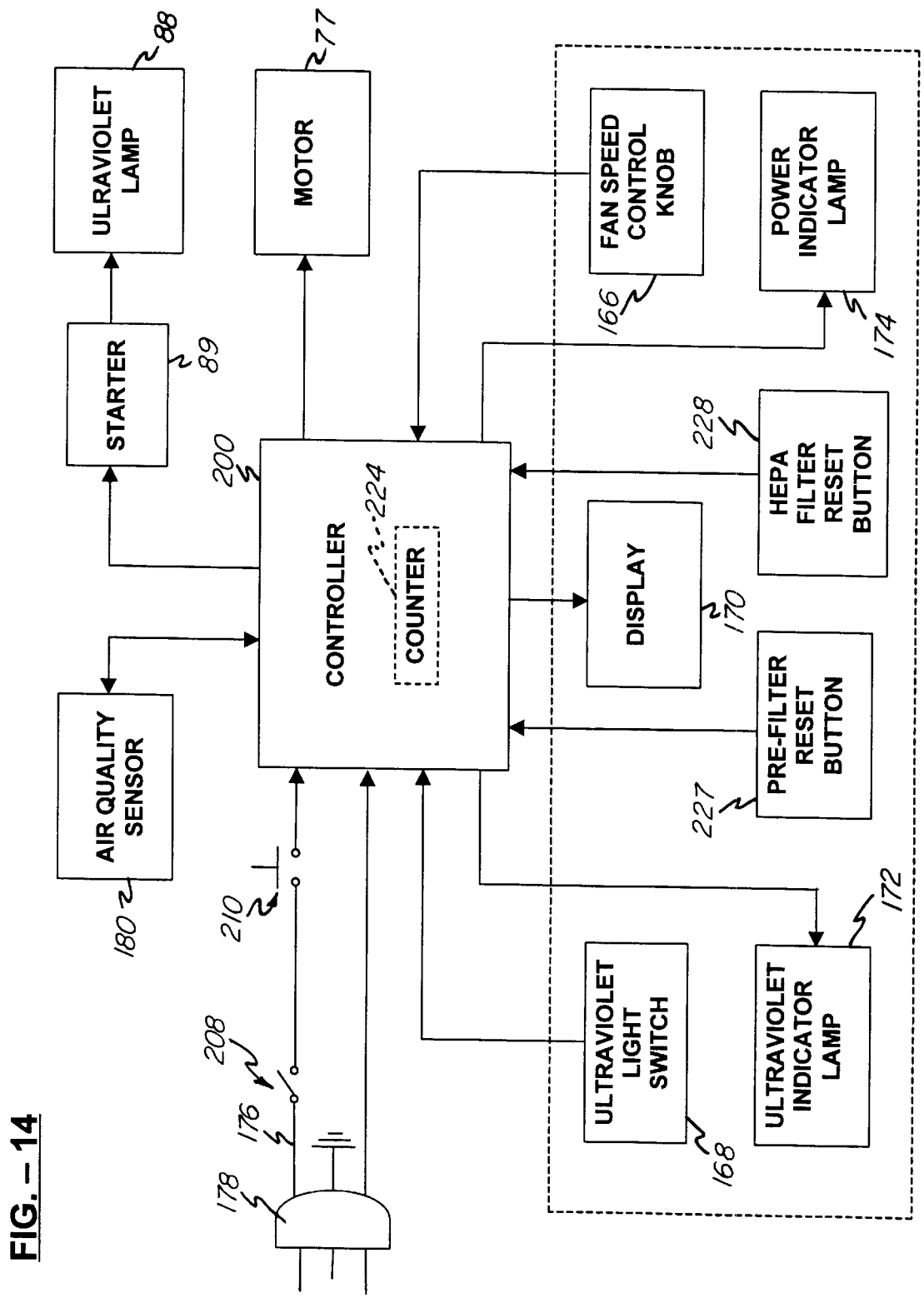
FIG. 14 is a block diagram illustrating the interconnection of various electrical components in a preferred embodiment of air purifier of the present invention.

The ultraviolet light source 86 either sterilizes or kills substantially all of the airborne micro-organisms which have not been entrained by the air filter assembly 38. More particularly, the UV light source 86 preferably comprises an ultraviolet C-band (UVC) lamp 88 which is positioned above the scroll wall 33. The ultraviolet lamp 88 most preferably generates a wavelength of 254 nanometers within the C-band range of wavelengths, such wavelength selected to effectively sterilize or kill micro-organisms while minimizing ozone production. In the most preferred embodiment, the UV lamp 88 is designated as type G6T5, wherein the G indicates a germicidal lamp, 6 designates the wattage and T5 designates the relative tubular diameter of the lamp 88 as equal to ⅝ths of an inch. The UV lamp 88 includes conventional ballast (not shown) and is connected to a starter 89 (FIGS. 2 and 14).

The lamp 88 includes an elongated tube 90 having opposing two-peg plugs 92 and 94, as is well known in the art. The plugs 92 and 94 are received within conventional lamp sockets 96 and 98. As known in the art, the plugs 92 and 94 and the sockets 96 and 98 differ from traditional household lighting fixtures and thereby prevent a user from accidentally using the lamp 88 in an inappropriate fixture. The sockets 96 and 98 are supported by a bracket 100 connected to an upper portion of the scroll wall 26. The bracket 100 is preferably composed of metal so that it will not be adversely impacted by ultraviolet light generated by the lamp 88.

A shield 102 is supported by the bracket 100 above the lamp 88 and includes an aperture 104 (FIGS. 7 and 8), the purpose of which is described below. The shield 102 assists in directing ultraviolet light inwardly toward the light chamber 18 and away from an outlet grille 106. It should be noted that the positioning of the ultraviolet lamp 88 downstream of the filter assembly 38 prevents the need for the periodic maintenance and cleaning of the lamp 88 since substantially no particles larger than 0.3 microns will pass through the HEPA filter 56.

With reference to FIGS. 6–9, the outlet grille 106 supported by the housing 12 within the air outlet 37 affords protection to users from exposure to potentially harmful ultraviolet light rays generated by the UV lamp 88. Moreover, the outlet grille 106 is designed to comply with the United States National Institute for Occupational Safety and Health's (NIOSH) standard for maximum permissible ultraviolet exposure of 0.4 micro-watts per centimeter squared ($\mu W/cm^2$) for a four hour exposure duration.

The outlet grille 106 includes a frame 108 supporting a plurality of substantially mutually horizontally spaced and vertically extending blades or slats 109 of conventional design separating a plurality of slots 110. The frame 108 includes a plurality of positioning tabs 112 for receipt within cooperating slots 114 formed within an upper wall 115 of the housing 12 (FIG. 8). Likewise, a pair of locking tabs 116 are supported by the housing 12 for lockingly and releasably engaging the frame 108. A handle 117 extends outwardly from the frame 108 to assist the user in removing the outlet grille 106 from the housing 12.

A louver assembly 118 is supported below the frame 108 and is substantially air permeable in that it permits for the passage of air from within the light chamber 18 out through the air outlet 37. However, the louver assembly 118 is substantially light impermeable in that it substantially prevents the passage of potentially harmful UV light supplied from the lamp 88 through the air outlet 37.

Figure 9:
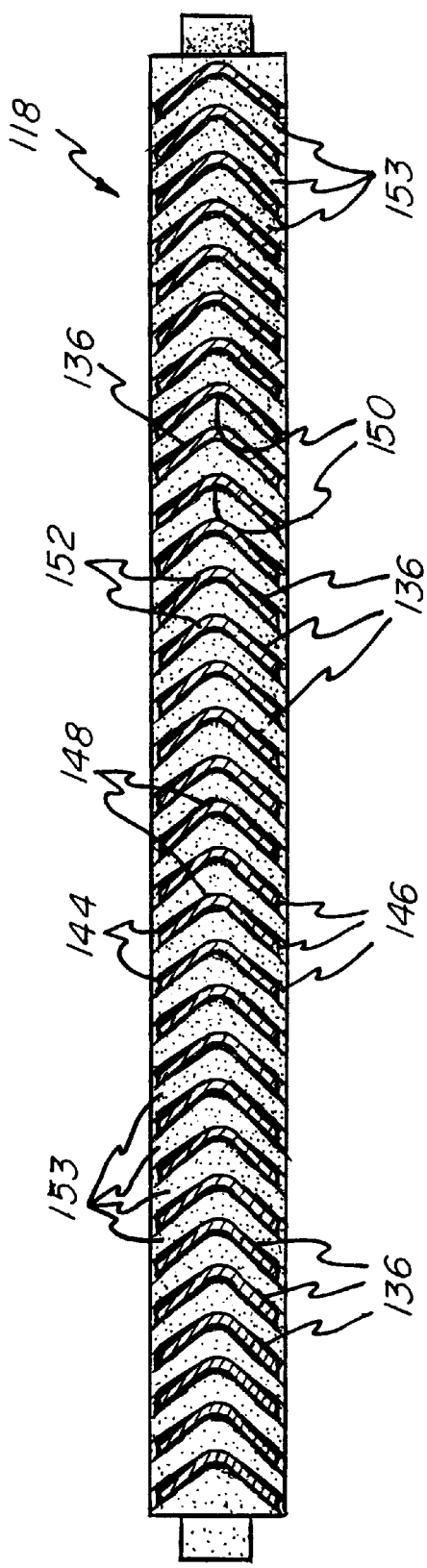
FIG. 9 is a cross-sectional view taken along line 9—9 of FIG. 8.

Referring now to FIGS. 8 and 9, the louver assembly 118 includes front and rear side support rails 120 and 122 secured to the frame 108 through a pair of brackets 124 and 126. The brackets 124 and 126 are secured to the frame 108 by conventional fasteners, such as bolts 128. The support rails 120 and 122 each include a plurality of arcuate grooves 130 for receiving opposing end edges 132 and 134 of a plurality of blades or slats 136. Each blade 136 includes a pair of opposing tabs 138 and 140 extending outwardly from the respective end edges 132 and 134 (FIG. 7). The tabs 138 and 140 are received within apertures 142 formed within the grooves 130 of the side rails 120 and 122 and then bent or deformed for securing the blades 136.

Each blade 136 includes a pair of opposing side edges 144 and 146 extending in a longitudinal direction between the opposing end edges 132 and 134. A center or mid portion 148 of each blade 136 extends between the opposing side edges 144 and 146. The blades 136 are arranged in an overlapping manner so that the side edges 144 and 146 of one blade 136 at least partially overlap the mid portion 148 of a second adjacent blade 136.

More particularly, each blade 136 includes a concave surface 150 and a convex surface 152 extending between the opposing side edges 144 and 146. The blades 136 are arranged in a manner such that each blade's concave surface 150 is positioned immediately proximate the adjacent blade's convex surface 152. As may be readily appreciated, this overlapping relationship defines a plurality of convoluted paths or channels 153 extending through the louver assembly 118 and thereby prevents the passage of ultraviolet light through a direct linear path. It should also be noted that the entire louver assembly 118 is preferably formed of a dark, light adsorbing color.

The blades 138 are preferably formed of metal and therefore resistant to damage from the UV light rays. The side rails 120 and 122 along with those portions of the housing 12, dividing wall 26, and scroll wall 33 forming the light chamber 18, are preferably composed of a thermoplastic material including a conventional ultraviolet light inhibitor to prevent ultraviolet damage thereto.

Turning now to FIGS. 7 and 8, a viewing window 154 is provided within the upper wall 115 of the housing 12 and is in visual communication with the UV lamp 88. Moreover, a viewing channel 158 extends between the viewing window 154 and the light chamber 18. The aperture 104 in the shield 102 provides direct visual access to the lamp 88. In order to protect the user from potentially harmful UV light rays, a cover 160 is provided within the window 154 for filtering UV light rays. The cover 160 is preferably formed of a polycarbonate material which is tinted to provide for easy visual indication of proper operation of the UV lamp 88.

Figure 3:
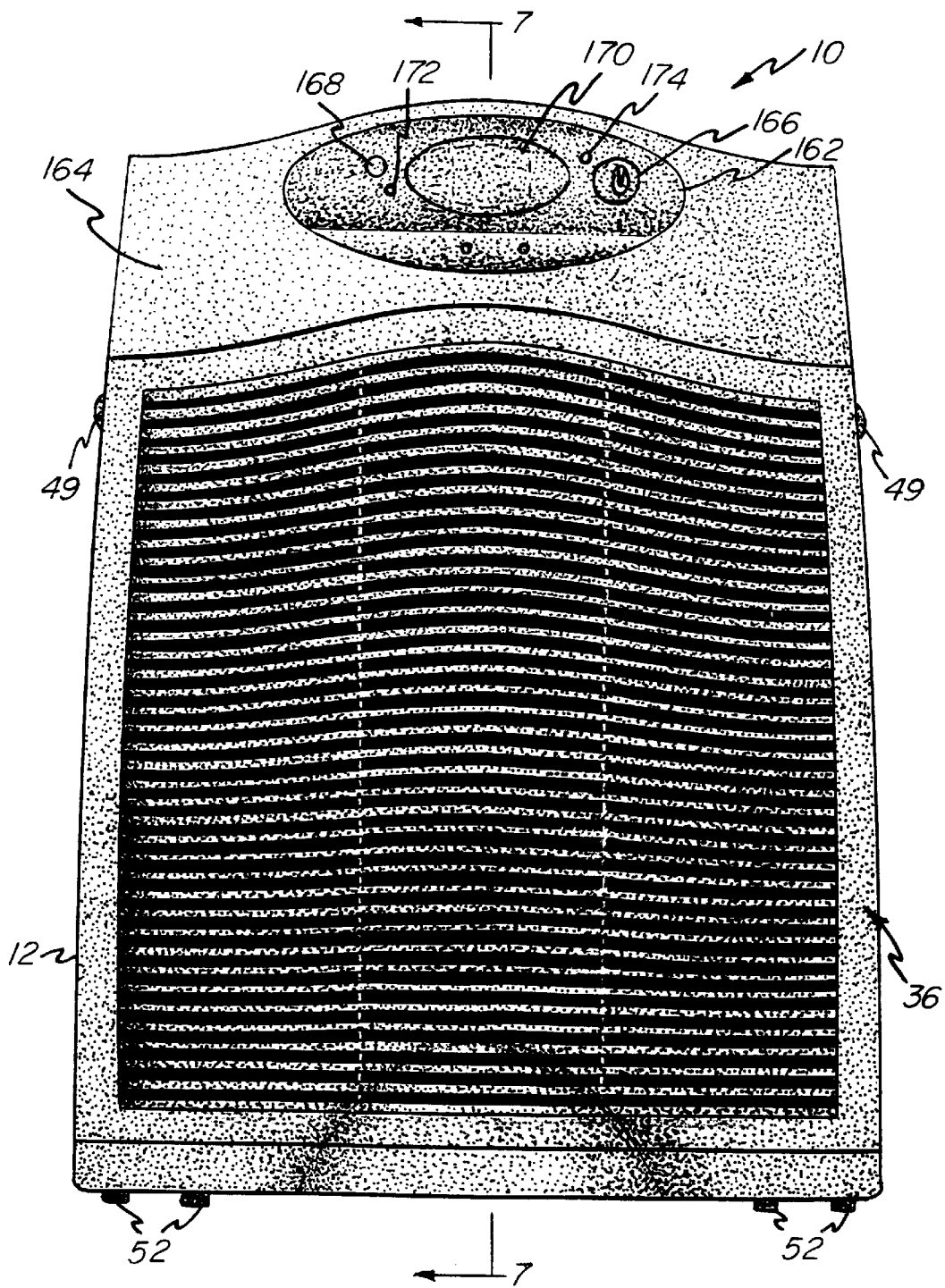
FIG. 3 is a front elevational view thereof.
Figure 4:
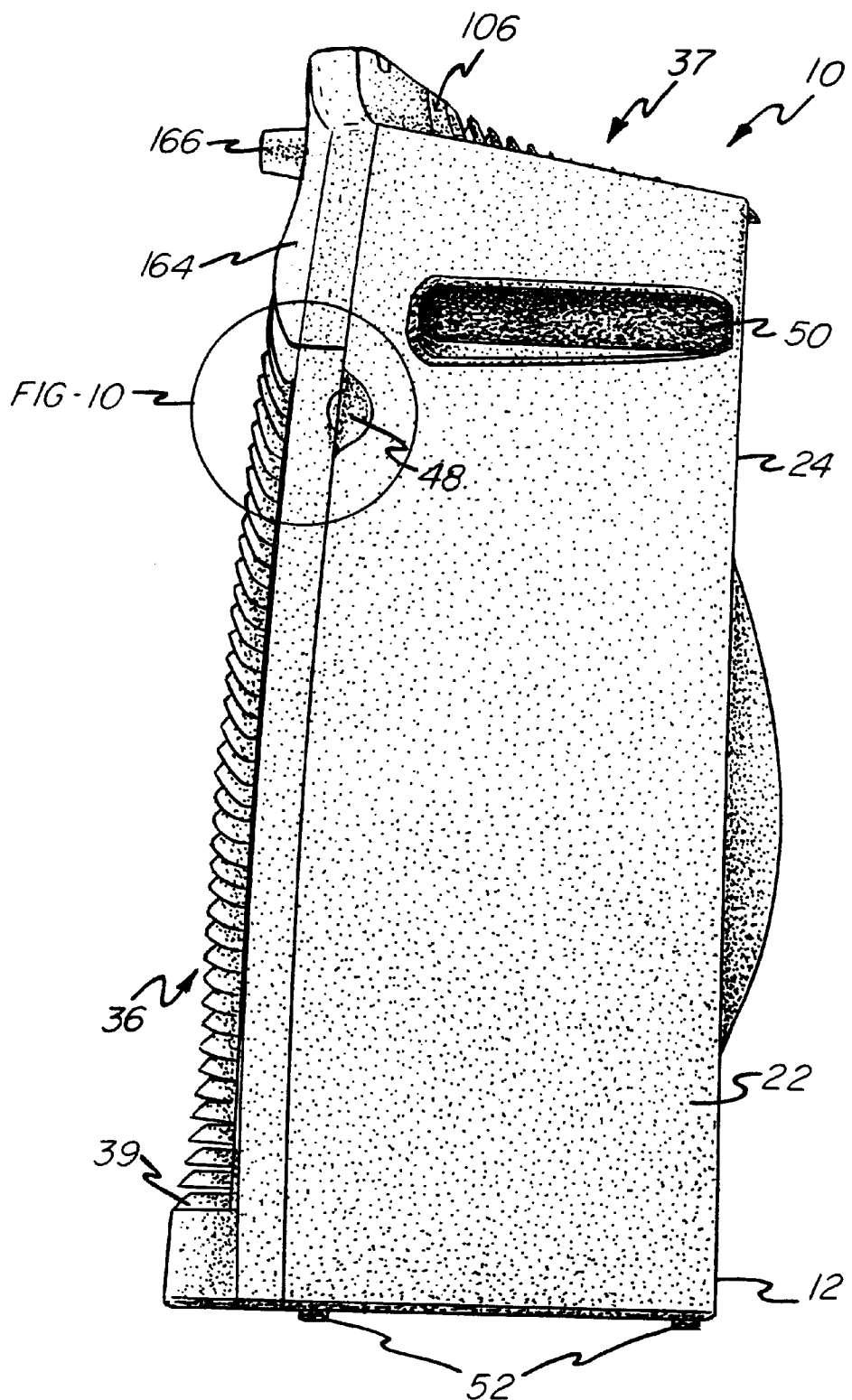
FIG. 4 is a right side elevational view thereof.
Figure 5:
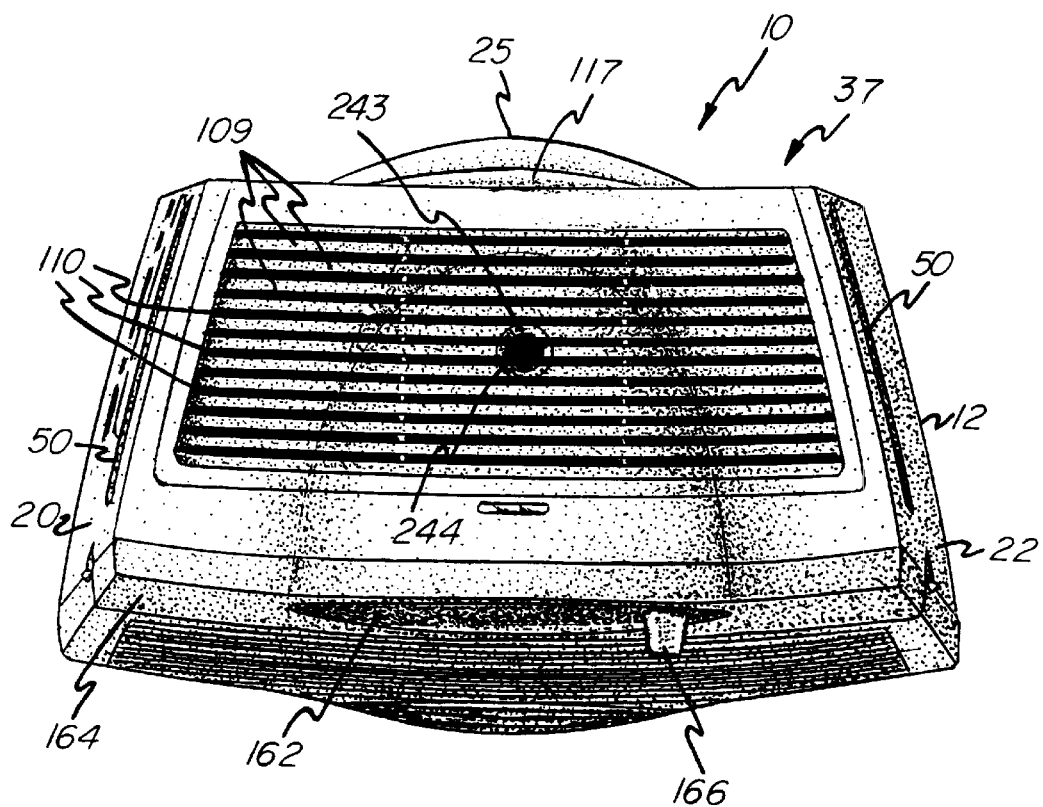
FIG. 5 is a top plan view thereof.
Figure 15:
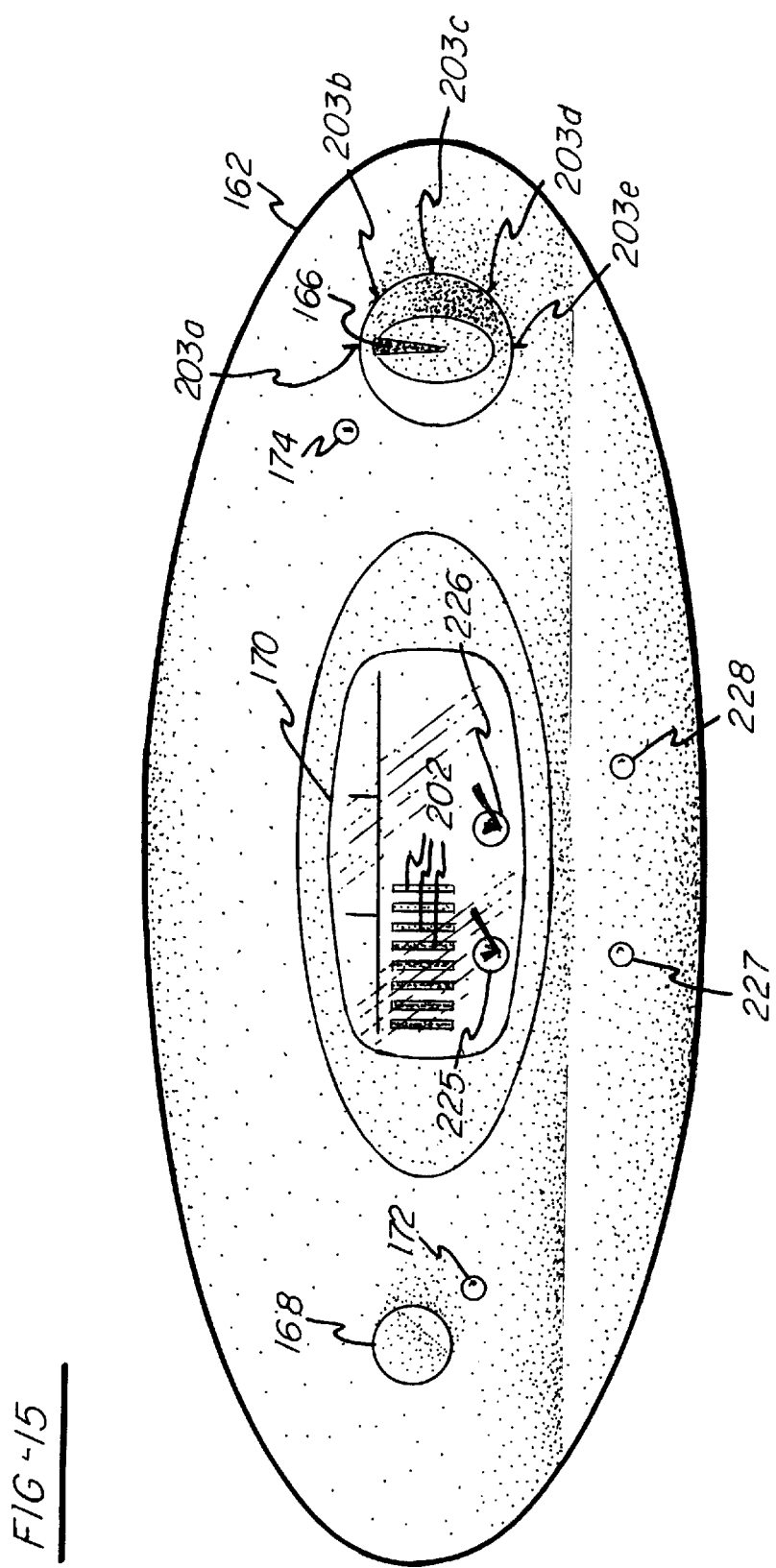
FIG. 15 is a detailed view of the control panel in a preferred embodiment of the air purifier of the present invention.

As illustrated in FIGS. 1, 3, and 15, an operating control panel 162 is preferably provided within a front wall 164 supported by the dividing wall 26. The control panel 162 includes a speed control knob 166 for controlling the speed of the fan motor 76, an ultraviolet violet light switch 168 for activating and deactivating the ultraviolet lamp 88 and a liquid crystal display (LCD) 170. An ultraviolet violet indicator lamp 172 and a power indicator lamp 174 are also provided within the control panel 162 and illuminate when the UV lamp 88 or the fan 78 are respectively activated.

A conventional electrical power cable 176 including a plug 178 supplies operating electric current to the various electrical components of the air purifier 10 including the electric motor 77 and the ultraviolet lamp 88 (FIGS. 6 and 14).

Figure 12:
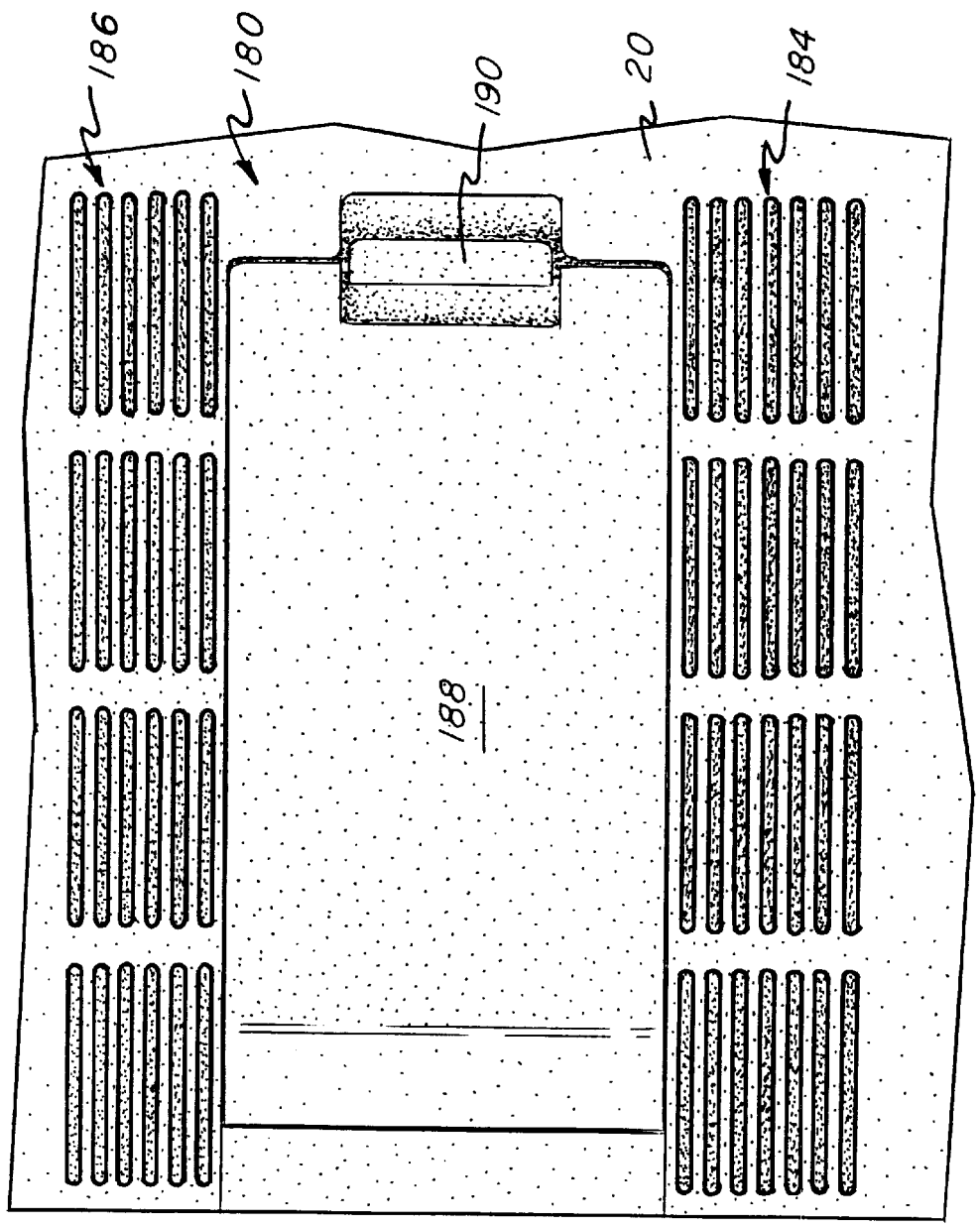
FIG. 12 is a detailed view of the left side of the air purifier of the present invention, showing the access door in a closed position and thereby covering the air quality sensor.
Figure 13:
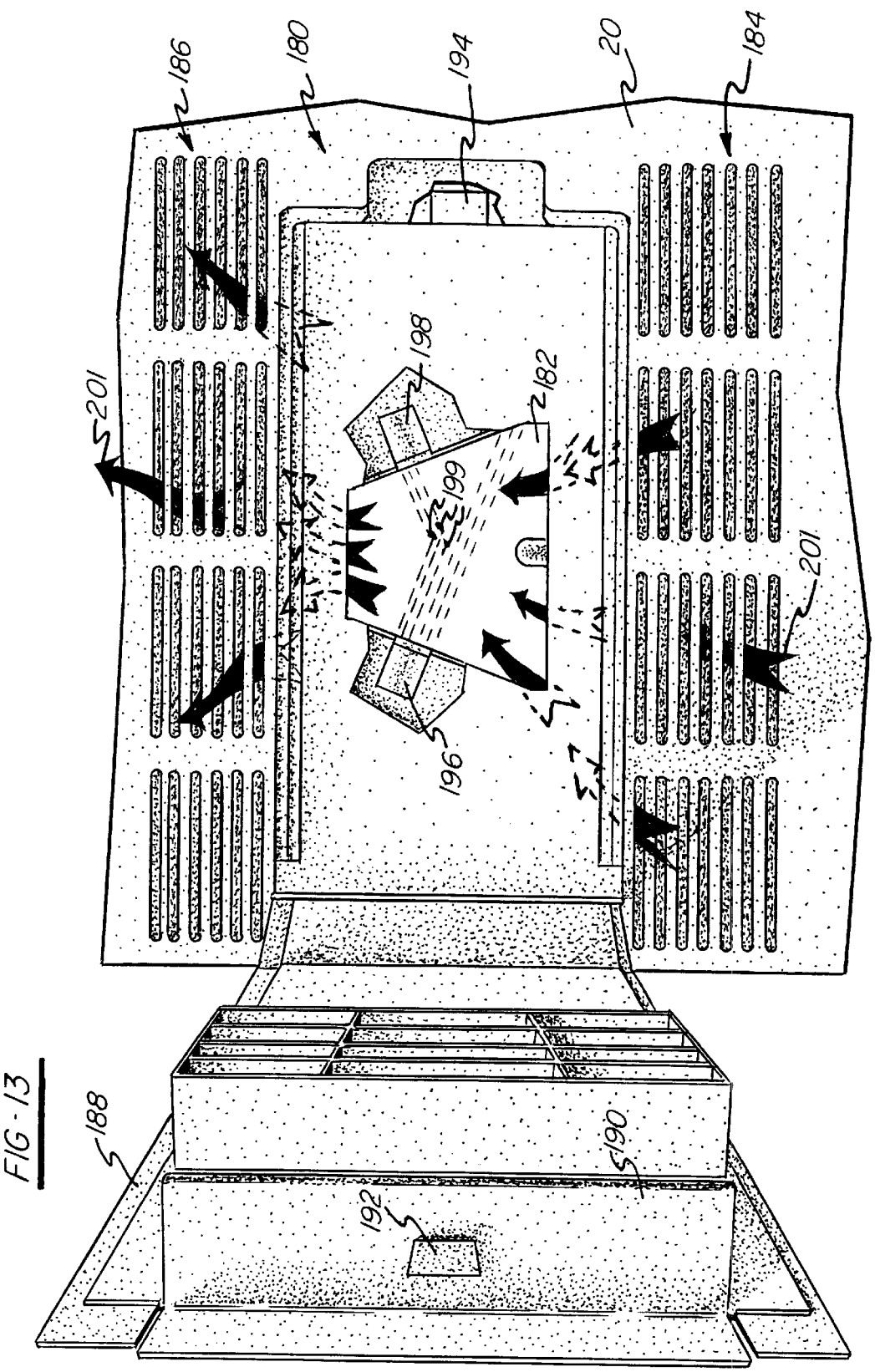
FIG. 13 is a detailed view of the left side of the air purifier of the present invention, showing the access door in an open position and thereby revealing the air quality sensor.

The liquid crystal display 170 provides an indication of the relative air quality of ambient air as received from an air quality sensor 180. Turning now to FIGS. 1, 12, and 13, the air quality sensor 180 is preferably supported within the left side wall 20 of the housing 12 and includes a sampling chamber 182 in fluid communication within an air inlet 184 and an air outlet 186 (FIG. 13). The sampling chamber 182 is accessible to the user through an access door 188 which is pivotally supported within the side wall 20. The access door 188 includes a resilient latch 190 including a biased tab 192 for engaging an aperture 194 formed in the side wall 20.

An infrared emitter 196 and an infrared receptor 198 are provided in communication within the sampling chamber 182. The infrared emitter 196 is disposed at an angle of approximately 90 degrees to the infrared receptor 198 wherein infrared light emitted from the emitter 196 is not directly received by the receptor 198. However, should the air within the sampling chamber 182 have particulates 199 entrained therein, then some of the infrared light transmitted by the emitter 196 will reflect off the particulates 199 and be at least partially received by the infrared receptor 198. As may be readily appreciated, the greater the number of particulates 199 within the air received in the sampling chamber 182, then the more infrared light will be received by the receptor 198.

A resistor (not shown) is provided proximate the air inlet 184 for generating heat which, by virtue of a chimney effect resulting from the rising of warm air, causes air to be drawn through the inlet 184 and into the sampling chamber 182. The air continues to flow upwardly out of the sampling chamber 182 and through the air outlet 186 as illustrated by arrows 201 in FIG. 13.

Turning now to FIGS. 14 and 15, the air quality sensor 180, based upon the amount of infrared light received by the receptor 198, provides an air quality signal to a controller 200, the air quality signal indicative of the ambient air quality. The controller 200 is in communication with the liquid crystal display 170 which, in turn, converts the air quality signal from the air quality sensor 180 to a number of indicator bars 202 displayed within the liquid crystal display 200. The number of indicator bars 202 displayed provides an indication of the ambient air quality. In the preferred embodiment, the greater the number of indicator bars 202 displayed, then the less the ambient air quality.

Furthermore, based upon the air quality signal provided by the air quality sensor 180, the controller 200 varies operation of the fan motor 77 when an automatic mode of operation is selected by the user through speed control knob 166. Moreover, the speed control knob 166 includes not only set positions for off, low, medium and high speeds, as indicated by reference numerals 203a, 203b, 203c, and 203d in FIG. 15, but an automatic set position 203e for instructing the controller 200 to automatically vary the speed of the fan motor 77 based upon the air quality signal provided by the sensor 180.

With further reference to Table I, should the air quality detected by the sensor 180 be poor, then the number of indicator bars 202 displayed is defined to be within the range of 13 to 18 and the controller 200 automatically selects a high operating speed for the fan motor 77. Should the air quality signal provided by the air quality sensor 180 indicate a fair ambient air quality, then the number of indicator bars 202 displayed by the liquid crystal display 170 is within the range of 7 to 12 and the controller 200 selects a medium operating speed for the fan motor 77. Finally, should the air quality signal provided by the sensor 180 indicate good ambient air quality, then the number of indicator bars 202 displayed by the liquid crystal display 170 is between 1 to 6 and the controller 200 automatically selects a low operating speed for the fan motor 77.

TABLE I

| Air Quality Signal Indication | Number of Indicator Bars | Controller Selected Fan Speed |
| --- | --- | --- |
| Poor | 13 to 18 | 3 - High |
| Fair | 7 to 12 | 2 - Medium |
| Good | 1 to 6 | 1 - Low |

As illustrated in FIG. 2, a cleaning device 204 is preferably provided for manually cleaning particulate from the lenses of the infrared emitter 196 and infrared receptor 198. The cleaning device 204 most preferably comprises a resilient sponge coated with a felt material, and has a cross-section slightly larger than the cross-section of the sampling chamber 182 for providing for a compression fit within the sampling chamber 182.

When not in use, the cleaning device 204 is stored within a storage compartment 206 positioned within the edge of the right side wall 29. The storage compartment 206 is hidden from view by the inlet grille 39 when the air purifier 10 is in use.

A further safety feature of the air purifier 10 of the present invention includes interlocking inlet and outlet safety switches 208 and 210. Moreover, as illustrated in FIGS. 2 and 10, a tab 212 extends inwardly from the frame 42 of the inlet grille 39 and is selectively engagable with a leaf or contact 214 of the inlet safety switch 208. The inlet safety switch 208 is mounted behind a slot 216 formed in the edge of the side wall 29 to prevent inadvertent contact therewith. The inlet safety switch 208 is of conventional design and is in a normally open condition. Thus, when the inlet grille 39 is removed, the contact 214 moves to open the inlet switch 208 so as to interrupt power to both the motor 77 and the ultraviolet lamp 88. When the inlet grille 39 is replaced in its proper position relative to the housing 12, the tab 212 engages the contact 214 thereby closing the inlet switch 208 and supplying power from the power cable 176 to the fan motor 77 and the ultraviolet lamp 88.

Figure 11:
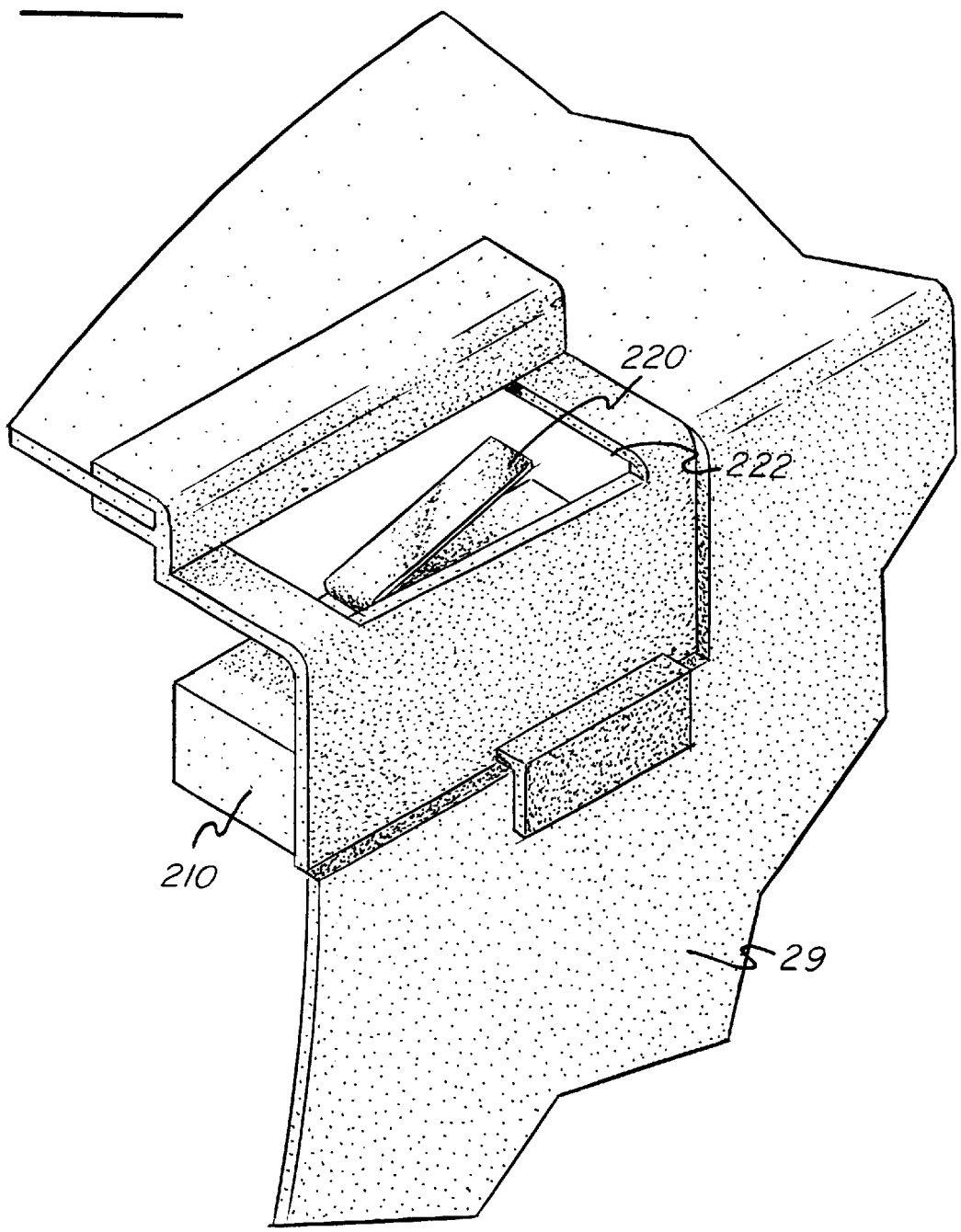
FIG. 11 is a detailed view of FIG. 8, showing the outlet grille safety switch.

Referring now to FIGS. 8 and 11, the outlet safety switch 210, designed similar to the inlet safety switch 208, is provided for ensuring proper placement of the outlet grille 106 on the housing 12. A tab 218 extends downwardly from the bracket 126 of the louver assembly 118 and is selectively engagable with a leaf or contact 220 of the outlet safety switch 210. The outlet safety switch 210 is mounted behind a slot 222 formed within the light chamber 18 to prevent inadvertent contact therewith. Again, the outlet safety switch 210 is of conventional design and is in a normally open position. Thus, when the outlet grille 106 including louver assembly 118 is removed, the contact 220 moves to open the outlet switch 210 so as to interrupt power to the ultraviolet lamp 88 and the motor 77.

As illustrated in FIG. 14, the inlet and outlet switches 208 and 210 are connected in series intermediate the power cable 176 and the rotary control knob 166. As long as the switches 208 and 210 are closed and the UV light switch 168 is closed, then power is supplied to the ultraviolet lamp 88. This power is shown coupled to the controller 200, the output of which couples to the lamp sockets 96 and 98 and the starter 89. If either one of the inlet and outlet switches 208 and 210 is open because the inlet or outlet grilles 39 and 106 are removed, then all power to the ultraviolet lamp 88 and fan motor 77 is disconnected.

Referring further to FIGS. 14 and 15, the controller 200 further includes a counter or timer 224 which maintains a count of cumulative operating time of the air purifier 10. After each of first predetermined time intervals has elapsed, then a "check pre-filter" indicator 225 within the liquid crystal display 170 signals to the user that the pre-filter 66 should be checked for replacement. When each of second predetermined time intervals has elapsed, a "check HEPA filter" indicator 226 within the liquid crystal display 170 instructs the user to check the HEPA filter 56 for replacement. The pre-filter 66 should require replacement more often than the HEPA filter 56 and, as such, the first predetermined time interval is defined to be significantly less than the second predetermined time interval.

A pre-filter reset button 227 and a HEPA filter reset button 228 are provided within the control panel 162 for resetting the counter 224 with respect to the pre-filter 66 elapsed operating time and the HEPA filter 56 elapsed operating time. When a user replaces either of the filters 66 and 56, he or she then depresses the appropriate reset button 227 and 228 for resetting the counter 224 to zero.

Figure 16:
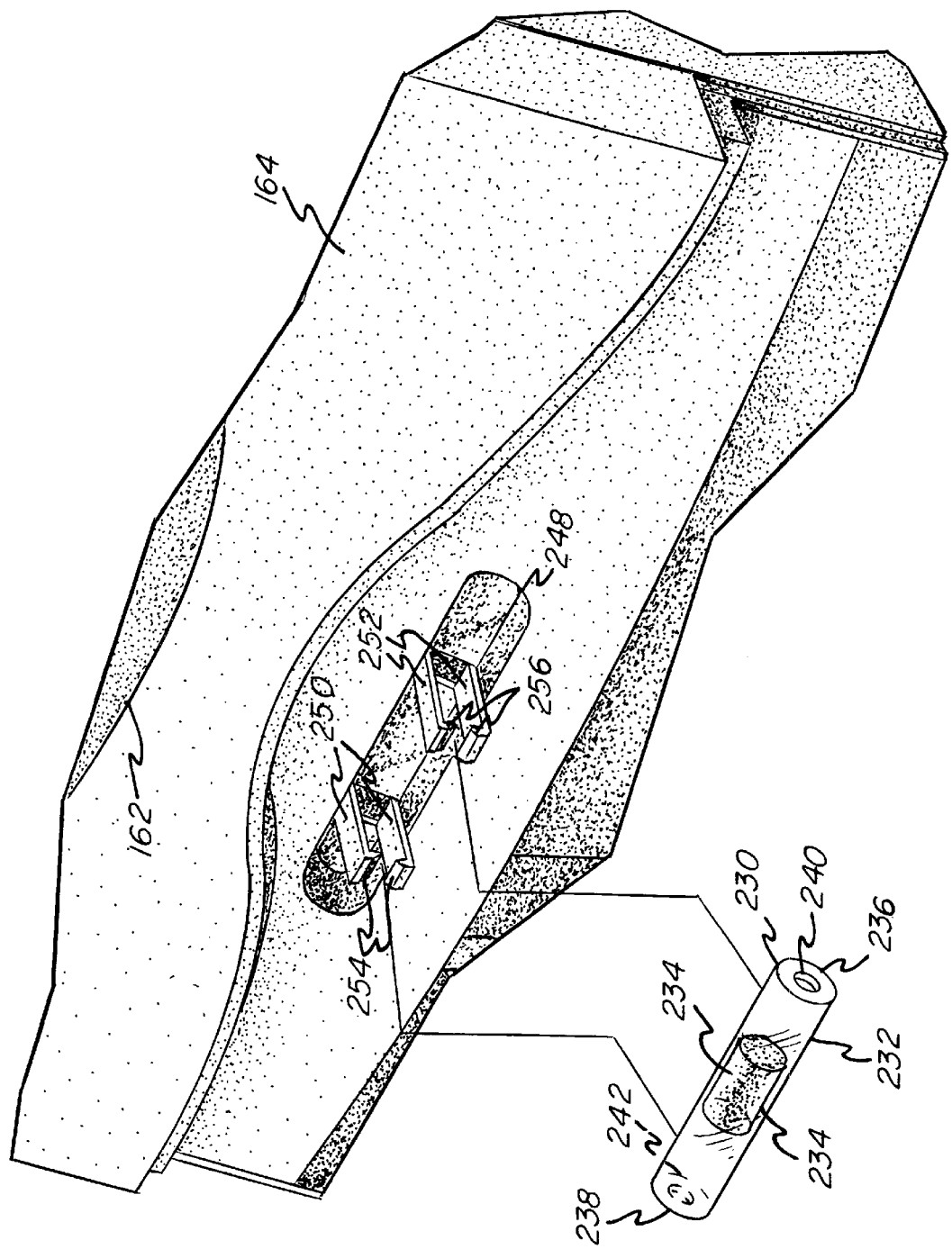
FIG. 16 is a fragmentary exploded perspective view of a filter check gauge and a filter check gauge storage compartment.

To facilitate the checking of the filters 66 and 56 after the pre-filter and the HEPA filter indicators 225 and 226 are activated, a filter check gauge 230 is provided as illustrated in FIGS. 2, 8, and 16. The filter check gauge 230 comprises a substantially transparent cylindrical tube 232 and a cylindrical indicator 234 slidably received within the tube 232. Opposing ends 236 and 238 of the tube 232 are preferably open. An annular lip 240 and 242 is positioned adjacent each end 236 and 238 of the tube 232 to prevent discharge of the indicator 234. The indicator 234 is preferably of a distinguishable color when positioned with the tube 232. Both the tube 232 and the indicator 234 are preferable molded from a thermoplastic material.

During operation, the filter check gauge 230 is removably supported by an annular shoulder 243 positioned within the lower portion of a recess 244 formed within the upper surface 246 of the outlet grille 106. Either end 236 and 238 of the filter check gauge 230 is positioned within the recess 244, and if the filters 66 and 56 are operating properly, then the indicator 234 will float up the filter check gauge 230. In use, the gauge 230 projects above the outlet grille 106 and air exiting the grille 106 exerts pressure against the indicator 234. The air pressure is converted to a lifting force which, when greater than the weight of the indicator 234, causes the indicator 234 to rise within the tube 232. If the indicator 234 does not move up within the gauge 230, then the filters 66 and 56 are most likely clogged with particulate and one or both should be replaced. As noted above, replacement of the filters 66 and 56 is a simple matter of removing the inlet grille 39 and pulling the filters from within the filtration chamber 14.

When the filter check gauge 230 is not being used, then it is conveniently stored within a compartment 248 formed within the housing 12 behind the inlet grille 39. The storage compartment 248 includes pairs of resilient arms 250 and 252 having lips 254 and 256 for releasably securing the tube 232 in position.

A particular benefit of the invention resides in the multiple stage cleaning by the air purifier 10. At a first level, immediately adjacent the air inlet 36, the particulate pre-filter 66 captures relatively large airborne particulates, such as pollen, mold, smoke, dust, and pet dander while the carbon therein absorb and oxidizes odors, gases and chemicals. The pre-filter 66 compliments the micro-filtration HEPA media 60 of the primary filter 56 which traps particulates down to a size of 0.3 microns. Micro-organisms that pass through the HEPA filter 56 are then killed or sterilized by the germicidal ultraviolet lamp 88.

In operation, a user activates the air purifier 10 by rotating the motor speed control knob 166 from the off position 203a to a desired speed setting 203b, 203c, 203d, or alternatively, to the automatic function setting 203e (FIG. 15). Should the user select the automatic function setting 203e, then the air quality sensor 180 reads the ambient air quality from air drawn into the sampling chamber 182. More particularly, the amount of infrared light received by the receptor 198 provides an indication of the air quality based upon the number of particulates 199 contained therein. An air quality signal is then sent from the air quality sensor 180 to the controller 200. Based upon the air quality signal, the controller 200 varies the speed of the motor 77 driving the fan 78.

The fan 78 causes ambient air to be drawn axially through the air inlet 36 and initially flow through the pre-filter 66 for removing relatively large particulates. In the next stage, the air is further cleaned wherein particulates down to the size of 0.3 microns are removed by the HEPA filter 56. The thus cleaned air flows through the housing 12 from the filtration chamber 14 to the blower chamber 16 and then into the ultraviolet light chamber 18 by operation of the fan 78. Within the ultraviolet light chamber 18, the ultraviolet lamp 88 sterilizes or kills substantially all remaining micro-organisms which may have passed through the filter assembly 38. The cleaned air is then passed through the outlet grille 106. As explained in greater detail above, the outlet grille 106 permits the passage of air but does not permit the passage of damaging ultraviolet light rays.

Accordingly, it may be appreciated that the air purifier 10 of the present invention provides for a portable self contained unit providing for multiple stage cleaning of ambient air through filtration and ultraviolet radiation while providing protection to the user from potentially damaging ultraviolet light rays.

While the form of apparatus herein describe constitutes the preferred embodiment of this invention, it is to be understood that the invention is not limited to this precise form of apparatus, and the changes may be made therein without departing from the scope of the invention which is defined in the appended claims.

What is claimed is:

1. An air purifier comprising:
   a housing supporting an air inlet, an air outlet and an air flow passage interconnecting said air inlet and said air outlet;
   a blower assembly supported within said housing for forcing air through said air flow passage from said air inlet to said air outlet;
   an ultraviolet light source comprised of an ultraviolet lamp oriented in a plane substantially perpendicular to and disposed in said air flow passage and positioned proximate said air outlet;
   a first air filter disposed in said air flow passage intermediate said air inlet and said ultraviolet light source; and
   an outlet grille supported by said housing proximate said air outlet, said outlet grille permeable to air and substantially impermeable to ultraviolet light.

2. The air purifier of claim 1 further comprising a window in visual communication with said ultraviolet light source, said window including a cover for filtering ultraviolet light.

3. An air purifier comprising:
   a housing supporting an air inlet, an air outlet and an air flow passage interconnecting said air inlet and said air outlet;
   a blower assembly supported within said housing for forcing air through said air flow passage from said air inlet to said air outlet;

an ultraviolet light source disposed in said air flow passage and positioned proximate said air outlet;

a first air filter disposed in said air flow passage intermediate said air inlet and said ultraviolet light source;

an outlet grille supported by said housing proximate said air outlet, said outlet grille permeable to air and substantially impermeable to ultraviolet light;

an outlet safety switch engageable with said outlet grille, said outlet safety switch operably connected to said ultraviolet light source for selectively deactivating said ultraviolet light source;

an inlet grill supported proximate said air inlet; and an inlet safety switch engageable with said inlet grille, said inlet safety switch operably connected to said blower assembly for selectively deactivating said blower assembly.

4. An air purifier comprising:

a housing supporting an air inlet, an air outlet and an air flow passage interconnecting said air inlet and said air outlet;

a blower assembly supported within said housing for forcing air through said air flow passage from said air inlet to said air outlet;

an ultraviolet light source disposed in said air flow passage and positioned proximate said air outlet;

a first air filter disposed in said air flow passage intermediate said air inlet and said ultraviolet light source;

an outlet grille supported by said housing proximate said air outlet, said outlet grille permeable to air and substantially impermeable to ultraviolet light;

a securing device supported by said first filter; and a second filter removably supported by said securing device of said first filter.

5. The air purifier of claim 4 wherein said first filter comprises a HEPA filter and said second filter comprises a carbon mesh filter, said HEPA filter positioned downstream from said carbon mesh filter.

6. An air purifier comprising:

a housing supporting an air inlet, an air outlet and an air flow passage interconnecting said air inlet and said air outlet;

a blower assembly supported within said housing for forcing air through said air flow passage from said air inlet to said air outlet, said blower assembly comprises a motor and a centrifugal fan operably connected to said motor, said centrifugal fan having a rotational axis substantially coaxially aligned with an inlet airflow;

an ultraviolet light source disposed in said air flow passage and positioned proximate said air outlet;

a first air filter disposed in said air flow passage intermediate said air inlet and said ultraviolet light source; and an outlet grille supported by said housing proximate said air outlet, said outlet grille permeable to air and substantially impermeable to ultraviolet light.

7. An air purifier comprising:

a housing supporting an air inlet, an air outlet and an air flow passage interconnecting said air inlet and said air outlet;

a blower assembly supported within said housing for forcing air through said air flow passage from said air inlet to said air outlet;

an ultraviolet light source disposed in said air flow passage and positioned proximate said air outlet;

a first air filter disposed in said air flow passage intermediate said air inlet and said ultraviolet light source;

an outlet grille supported by said housing proximate said air outlet, said outlet grille permeable to air and substantially impermeable to ultraviolet light;

a controller operably connected to said blower assembly for controlling movement of air through said air passage;

an air quality sensor including a sampling chamber that is separate from the air flow passage supported by said housing, an optical emitter communicating with said sampling chamber, an optical receptor communicating with said sampling chamber for detecting light emitted from said optical emitter; and wherein said air quality sensor provides a signal indicative of air quality within said sampling chamber to said controller, said controller selectively adjusting operation of said blower assembly in response to said signal.

8. The air purifier of claim 7 further comprising:

a cleaning member adapted to be removably received within said sampling chamber for cleaning said optical emitter and said optical receptor; and a storage compartment supported by said housing for removably storing said cleaning member.

9. An air purifier comprising:

a housing supporting an air inlet, an air outlet and an air flow passage interconnecting said air inlet and said air outlet;

a blower assembly supported within said housing for forcing air through said air flow passage from said air inlet to said air outlet;

an ultraviolet light source disposed in said air flow passage and positioned proximate said air outlet;

a first air filter disposed in said air flow passage intermediate said air inlet and said ultraviolet light source;

an outlet grille supported by said housing proximate said air outlet, said outlet grille permeable to air and substantially impermeable to ultraviolet light; and a filter check gauge removably positioned proximate said air outlet for providing an indication of air flow.

10. The air purifier of claim 9 further comprising a storage compartment supported by said housing for removably storing said filter check gauge.

11. An air purifier comprising:

a housing supporting an air inlet, an air outlet and an air flow passage interconnecting said air inlet and said air outlet;

a blower assembly supported within said housing for forcing air through said air flow passage from said air inlet to said air outlet;

an ultraviolet light source disposed in said air flow passage and positioned proximate said air outlet; and an outlet grille supported by said housing proximate said air outlet, said outlet grille including a plurality of substantially aligned blades, a plurality of convoluted paths defined intermediate said plurality of blades and permitting passage of air from said air flow passage through said air outlet while substantially preventing the passage of ultraviolet light from said ultraviolet light source through said air outlet.

12. The air purifier of claim 11 wherein:

each said blade includes a body having opposing longitudinally extending side edges and a longitudinally extending mid portion intermediate said side edges; and said side edges of each said blade overlap laterally with said mid portion of an adjacent one of said blades.

13. The air purifier of claim 11 wherein:

said outlet grille further comprises a pair of substantially parallel side rails; and each said blade includes a body having opposing end edges, and tabs extending outwardly from said end edges and secured to said side rails.

14. The air purifier of claim 11 wherein each said blade includes a body having opposing concave and convex outer surfaces, said concave outer surface positioned adjacent said convex surface of an adjacent blade.

15. The air purifier of claim 11 further comprising a first air filter disposed in said air flow passage intermediate said air inlet and said ultraviolet light source.

16. An air purifier comprising:

a housing supporting an air inlet, an air outlet and an air flow passage interconnecting said air inlet and said air outlet;

a blower assembly supported within said housing for forcing air through said air flow passage from said inlet end to said outlet end;

an air filter disposed in said air flow passage; and a filter check gauge removably positioned proximate said air outlet for providing an indication of volume of air flow.

17. The air purifier of claim 16 further comprising a storage compartment supported by said housing for storing said filter c heck gauge.

18. The air purifier of claim 16 further comprising an outlet grille supported by said housing proximate said air outlet and including a recess for removably receiving said filter check gauge.

19. The air purifier of claim 16 wherein said filter check gauge comprises a cylindrical tube and an indicator slidably received within said cylindrical tube for movement in response to air flow through said filter check gauge.

\* \* \* \* \*